(12) United States Patent
Zangen et al.

(10) Patent No.: US 9,254,394 B2
(45) Date of Patent: Feb. 9, 2016

(54) CENTRAL BASE COILS FOR DEEP TRANSCRANIAL MAGNETIC STIMULATION

(71) Applicant: BRAINSWAY LTD., Jerusalem (IL)

(72) Inventors: Abraham Zangen, Jerusalem (IL); Yiftach Roth, Rechelim (IL)

(73) Assignee: BRAINSWAY, LTD., Jerusalem (IL)

( * ) Notice: Subject to any disclaimer, the term of this patent is extended or adjusted under 35 U.S.C. 154(b) by 266 days.

(21) Appl. No.: 13/772,442

(22) Filed: Feb. 21, 2013

(65) Prior Publication Data
US 2014/0235928 A1    Aug. 21, 2014

(51) Int. Cl.
*A61N 2/02* (2006.01)
*A61N 2/00* (2006.01)

(52) U.S. Cl.
CPC *A61N 2/02* (2013.01); *A61N 2/006* (2013.01); *A61N 2/008* (2013.01)

(58) Field of Classification Search
CPC ......... A61N 2/02; A61N 2/006; A61N 2/008; A61N 1/36025; A61N 2/004; A61N 1/36021; A61N 2007/0026; A61N 1/36082; A61N 1/303
See application file for complete search history.

(56) References Cited

U.S. PATENT DOCUMENTS

| | | |
|---|---|---|
| 4,994,015 A | 2/1991 | Cadwell |
| 4,996,479 A | 2/1991 | Hoenig |
| 5,078,674 A | 1/1992 | Cadwell |
| 5,116,304 A | 5/1992 | Cadwell |
| 5,738,625 A | 4/1998 | Gluck |
| 6,066,084 A | 5/2000 | Edrich et al. |
| 6,179,771 B1 | 1/2001 | Mueller |
| 6,402,678 B1 | 6/2002 | Fischell et al. |
| 6,926,660 B2 | 8/2005 | Miller |
| 7,087,008 B2 | 8/2006 | Fox et al. |
| 7,407,478 B2 | 8/2008 | Zangen et al. |
| 7,976,451 B2 | 7/2011 | Zangen et al. |
| 7,998,053 B2 | 8/2011 | Aho |
| 8,267,850 B2 | 9/2012 | Schneider et al. |
| 8,277,371 B2 | 10/2012 | Zangen et al. |
| 8,388,510 B2 | 3/2013 | Zangen et al. |
| 8,523,753 B2 | 9/2013 | Schneider et al. |

(Continued)

FOREIGN PATENT DOCUMENTS

| | | |
|---|---|---|
| EP | 0361137 | 4/1990 |
| EP | 0492263 | 7/1992 |

(Continued)

OTHER PUBLICATIONS

Bishop, M P., "Intracranial Self-Stimulation in Man", *Science* 140(3565), (1963),394-396.

(Continued)

*Primary Examiner* — Christine H Matthews
*Assistant Examiner* — Joshua D Lannu
(74) *Attorney, Agent, or Firm* — Daniel J. Swirsky; Ricki L. Simon; AlphaPatent Associates Ltd.

(57) ABSTRACT

A transcranial magnetic stimulation coil which is location-specific for medial brain regions or lateral brain regions is designed with multiple spaced apart stimulating elements having current flow in a first direction, and multiple return elements having current flow in a second direction which is opposite the first direction. The multiple stimulating elements are distributed around a central axis of the coil.

20 Claims, 35 Drawing Sheets

(56) References Cited

U.S. PATENT DOCUMENTS

| | | |
|---|---|---|
| 8,591,392 B2 | 11/2013 | Bentwich et al. |
| 8,608,634 B2 | 12/2013 | Zangen et al. |
| 8,657,731 B2 | 2/2014 | Riehl et al. |
| 8,723,628 B2 | 5/2014 | Mishelevich et al. |
| 2004/0078056 A1* | 4/2004 | Zangen et al. ............ 607/2 |
| 2005/0154426 A1 | 7/2005 | Boveja et al. |
| 2005/0228209 A1 | 10/2005 | Schneider et al. |
| 2006/0094924 A1 | 5/2006 | Riehl et al. |
| 2006/0129205 A1 | 6/2006 | Boveja et al. |
| 2006/0287566 A1* | 12/2006 | Zangen et al. ............ 600/15 |
| 2007/0293916 A1 | 12/2007 | Peterchev |
| 2010/0152522 A1 | 6/2010 | Zangen et al. |
| 2011/0184223 A1 | 7/2011 | Peterchev |

FOREIGN PATENT DOCUMENTS

| | | |
|---|---|---|
| EP | 0554880 | 8/1993 |
| EP | 0595227 | 5/1994 |
| WO | WO-91/02259 | 2/1991 |
| WO | WO-98/06342 | 2/1998 |
| WO | WO-02/32504 | 4/2002 |
| WO | WO-2010/017249 | 2/2010 |
| WO | WO-2010/067336 | 6/2010 |

OTHER PUBLICATIONS

Branston, N. M., "Analysis of the distribution of currents induced by a changing magnetic field in a volume conductor", *Phys. Med. Biol.* 36(2), (1991),161-168.

Branston, N. M., Tofts P.S., "Magnetic stimulation of a volume conductor produces a negligible component of induced current perpendicular to the surface", J Physiol (Lond). 1990;423:67.

Brasil-Neto, Joaquim P., "Optimal focal transcranial magnetic activation of the human motor cortex: effects of coil orientation, shape of the induced current pulse, and stimulus intensity", *Journal of Clinical Neurophysiology* 9(1), (1992),132-136.

Breiter, Hans C., "Acute effects of cocaine on human brain activity and emotion", *Neuron 19*, (1997),591-611.

Cadwell, John, "Optimizing magnetic stimulator design", *Magnetic Motor Stimulation: Principles and Clinical Experience 43*, (1991),238-248.

Cohen, David, "Developing a more focal magnetic stimulator, Part I: Some basic principles", *Journal of Clinical Neurophysiology* 8(1), (1991),102-111.

Cohen, Leonardo G., "Effects of coil design on delivery of focal magnetic stimulation. Technical considerations", *Electroencephalography and Clinical Neurophysiology 75*, (1990),350-357.

Deng, Zhi-De, "Coil Design Considerations for Deep-Brain Transcranial Magnetic Stimulation (dTMS)", 30th Annual International IEEE EMBS Conference Vancouver, British Columbia, Canada, Aug. 20-24, 2008, 5675-5679.

Eaton, H., "Electric field induced in a spherical volume conductor from arbitrary coils: application to magnetic stimulation and MEG", *Medical and Biological Engineering and Computing 30*, (Jul. 1992),433-440.

Enticott, Peter G. et al, "Deep Repetitive Transcranial Magnetic Stimulation Associated With Improved Social Functioning in a Young Woman With an Autism Spectrum Disorder", (J ECT 2011;27: 41-43).

Fadini, Tommaso et al., "H-coil: Induced electric field properties and input/output curves on healthy volunteers, comparison with a standard figure-of-eight coil", Clinical Neurophysiology 120 (2009) 1174-1182.

George, Mark S., "Transcranial Magnetic Stimulation", *Neurosurgery Clinics of North America 14*, (2003),283-301.

Hallett, Mark, "Transcranial magnetic stimulation and the human brain", *Nature 406*, (Jul. 2000),147-150.

Klein, Ehud, "Therapeutic efficacy of right prefrontal slow repetitive transcranial magnetic stimulation in major depression—a double-blind controlled study", *Arch. Gen. Psychiat. 56*, (1999),315-320.

Kranz, G., "Transcranial magnetic brain stimulation modulates blepharospasm", Neurology 75 (16), (2010), 1465-1471.

Kraus, Karl H., "The use of a cap-shaped coil for transcranial magnetic stimulation of the motor cortex", *Journal of Clinical Neurophysiology 10*, (1993),353-362.

Krause, Laura et al, "The role of medial prefrontal cortex in theory of mind: A deep rTMS study", Behavioural Brain Research [2012, 228(1):87-90].

Maccabee, P J., "Spatial distribution of the electric field induced in volume by round and figure '8' magnetic coils: relevance to activation of sensory nerve fibers", *Electroencephalography and Clinical Neurophysiology 76*, (1990),131-141.

Paus, Tomas, "Transcranial Magnetic Stimulation during Positron Emission Tomography: A New Method for Studying Connectivity of the Human Cerebral Cortex", *Journal of Neuroscience 17*, (1997),3178-3184.

Ren, Chunye, "A novel electric design for electromagnetic stimulation—the slinky coil", *IEEE Transactions on Biomedical Engineering 42*(9), (Sep. 1995),918-925.

Roth, Yiftach, "A coil design for transcranial magnetic stimulation of deep brain regions", *Journal of Clinical Neurophysiology 19*(4), (2002),361-370.

Ruohonen, J, "Focusing and targeting of magnetic brain stimulation using multiple coils", *Medical and Biological Engineering and Computing*, (1998),297-301.

Thielscher, Axel et al., "Linking Physics with Physiology in TMS: A Sphere Field Model to Determine the Cortical Stimulation Site in TMS", NeuroImage 17, 1117-1130 (2002) doi:10.1006/nimg.2002. 1282.

Tofts, P.S., "The Distribution of Induced Currents in Magnetic Stimulation of the Nervous System", *Phys. Med. Biol. 35*(8),(1990),1119-1128.

Tofts, P.S., "The Measurement of Electric Field, and the Influence of Surface Charge, in Magnetic Stimulation", *Electroencephalography and Clinical Neurophysiology 81*, (1991),238-239.

Yunokuchi, Kazutomo, "Developing a more focal magnetic stimulator, Part II: Fabricating coils and measuring induced current distributions", *Journal of Clinical Neurophysiology 8*(1), (1991),112-120.

Zangen, Abraham, "Transcranial magnetic stimulation of deep brain regions: evidence for efficacy of the H-coil", *Clinical Neurophysiology 116*, (2005),775-779.

Zimmermann, Kuno P., "Slinky coils for neuromagnetic stimulation", *Electroencephalography and Clinical Neurophysiology 101*, (1996),145-152.

* cited by examiner

CENTRAL BASE COILS FOR DEEP TRANSCRANIAL MAGNETIC STIMULATION

FIELD OF THE INVENTION

The present invention relates to a family of deep transcranial magnetic stimulation (TMS) coils for stimulating medial or lateral brain regions.

BACKGROUND OF THE INVENTION

Transcranial magnetic stimulation (TMS) is a noninvasive technique used to apply brief magnetic pulses to the brain, or to other human organs, and to thereby activate neuronal structures. The pulses are administered by passing high currents by a stimulator through an electromagnetic coil externally placed upon the patient (for example, placed on the scalp for brain treatment), inducing electrical currents in the underlying tissue, thereby producing a localized axonal depolarization. This technique has become a major tool in central nervous system research, as well as a potentially promising treatment option for various neurobehavioral and neurological disorders.

Most known TMS coils stimulate superficial brain regions in the brain cortex, but the rate of decay of the induced magnetic and electric field as a function of distance from the coil is high. Hence the efficacy of affecting deeper neuronal structures is low. Stimulating deeper neuronal structures may be feasible if the intensity of the induced field is greatly increased. Yet operation at such increased intensity may increase the risk for seizures and for physiological damage to the tissue.

A method for deep brain TMS with minimal stimulation of superficial regions is disclosed in U.S. Pat. No. 7,407,478, wherein deep brain stimulation is made possible while minimizing side effects. The device described therein includes a base and an extension portion, the base having individual windings for individual paths of current flow, and the extension portion designed so as to minimize unwanted stimulation of other regions of the brain.

However, there is a need for more specifically designed coils, which can target particular areas of the brain including deep neuronal structures with minimal effect on other brain regions. Examples of specific brain regions that may be desired to be stimulated are medial brain regions including the anterior cingulate cortex, medial prefrontal cortex, medial motor cortex, the supplementary motor area (SMA), the premotor area (PMA), the posterior cingulate cortex, and regions in the preconeus. Other examples may include lateral brain regions such as the lateral prefrontal cortex, the insula, the entorhinal cortex, temporal cortex regions and the fusiform face area (FFA).

Thus, there is a need for specifically designed coils for deep TMS which are location-specific for medial brain regions or lateral brain regions. The coils must induce the desired distribution of the electric field in the brain, and simultaneously induce electric field intensity in the relevant brain tissue which will be feasible for neuronal stimulation with available TMS stimulators for most of the population. The stimulation intensity is routinely calibrated individually for each subject based on his or her motor threshold. Hence the coil efficiency must guarantee that the motor threshold and stimulation intensity for most of the relevant population is within an acceptable range with respect to available stimulators power outputs.

The coils design must be efficient with respect to energy consumption, coil heating rate, compact size and ease of operation.

SUMMARY OF THE INVENTION

There is provided, in accordance with one embodiment of the present invention, a coil for transcranial magnetic stimulation. The coil includes a base portion having a central axis defining a base portion right side on a right side of the central axis and a base portion left side on a left side of the central axis, multiple right side stimulating elements positioned in the base portion right side, configured to carry electrical current in a first direction, multiple left side stimulating elements positioned in the base portion left side, configured to carry electrical current in the same first direction. The coil further includes a return portion having multiple right side return elements, wherein each of the right side return elements corresponds to one of the multiple right side stimulating elements, and wherein each of the multiple right side return elements is configured to carry electrical current in a second direction which is opposite the first direction, and multiple left side return elements, wherein each of the left side return elements corresponds to one of the multiple left side stimulating elements, and wherein each of the multiple left side return elements is configured to carry electrical current in the second direction, wherein the return portion is spaced a distance away from said base portion.

In embodiments of the present invention, the base portion is complementary to the human head or head portion, or to another body organ. The base has a flexibility that allows it to conform to the relevant body organ (such as the human head or head portion).

The base includes individual elements carrying electric current in one or more common directions, referred to herein as a "main direction." In this main direction, the main physiologic effect (such as neuronal stimulation) is induced in the body organ. The elements are not dense together at a narrow segment, but are rather distributed at various locations around the body organ. In some embodiments the individual elements are evenly distributed across the base. In other embodiments some or all the elements may be grouped in two or more groups with certain distances between the groups. The spacing between adjacent elements may be uniform, variable, periodic or other. In embodiments where some or all the elements are grouped in groups, the spacing between adjacent groups or between a group and an adjacent element, and the breadth of each group, may be uniform across the base, variable, periodic or other. Any combination or arrangement of elements is included within the scope of the invention, with a particular feature being that the elements are not crowded together in a narrow segment.

The individual elements in the base carrying current in the main direction are all or mostly tangential to the relevant body organ (such as a portion of a human skull), at all or a substantial part of their path. In order to optimize the efficacy of activation in deeper brain regions, it is desirable to minimize the non-tangential components of the induced electric field. Since the induced electric field orientation is in general parallel to the orientation of the elements carrying alternating currents, it is desirable to minimize the portions of coil elements which are non-tangential to the body organ (such as a human skull), especially in the base and its vicinity.

Coil elements carrying electric current in a direction opposite to the one or more main directions, are placed remote from the base. These elements are referred to herein as "return elements." In some embodiments, the return elements are located adjacent to other body organs or other portions of a body organ (such as other head regions), relative to the base. These return elements are termed "contacting return elements." In other embodiments, the return elements are located at a certain distance from the body and are not configured to contact the body. These return elements are termed "protruding return elements." In some embodiments, some of the return elements are contacting and some of them are protruding.

Return elements may be located on more than one side of the base. In some embodiments, the coil includes return elements on two sides of the base. In other embodiments, the coil includes return elements on three or more sides of the base. As an example, a certain embodiment may include a central medial base located over a human medial cortex, and two groupings of return elements located to the left and to the right of the central base. In some embodiments, these return elements are contacting and adjacent to lateral cortical regions. In other embodiments these return elements are protruding and located at a distance from any brain region. In yet other embodiments, some of the return elements are contacting and some are protruding. In some embodiments all the return elements on one side of the base—i.e. left—are contacting, while all the return elements on the other side are protruding. In yet other embodiments, each side of the base—i.e. left and right—includes both contacting and protruding return elements. In yet other embodiments, one side of the base—i.e. right—includes both contacting and protruding return elements, while the other side includes only contacting or only protruding return elements.

The definition of the base relates to the functional elements of the coil carrying electric currents. However, there is no limitation regarding other elements of the device, such as mechanical components, cases and covers. Thus, certain elements of the base may be encased in a case containing additional coil elements such as return elements and other elements. As an example, in a central base coil with a base placed over a medial cortex region, and having two lateral return portions to the left and to the right of the base, the base may include two groupings—left and right—of elements leading current in a main direction. In some embodiments the left group elements may be encased in a case together with the left return elements, and similarly for the right group in some embodiments. Hence mechanically the coil may be comprised of two portions—left and right—each of them having both central base elements and return elements. Yet, functionally the coil is comprised of a central base including elements leading currents in a main direction, and two return portions to the left and right of the base, including return elements leading currents in an opposite direction. Thus, the definitions of stimulating elements, return elements and connecting elements are based on the functionality of these elements or portions thereof.

The coil must induce the desired distribution of the electric field in the brain, and simultaneously induce an electric field intensity in the relevant brain tissue which is high enough to induce neuronal stimulation.

Several features of the coil are important in order to achieve the above goals. These include:

1. Arrangement of the base portion elements. This arrangement must be optimized for each coil design and each specific goal. An interplay between two competing ideals may take place: Better depth penetration profile, namely higher relative electric field in the deeper target brain region compared to superficial region, on one hand, and higher absolute electric field intensity in the target brain region on the other hand. As a non-limiting example, suppose a base portion contains two groups of elements with a certain distance d between them. Increasing d will improve the depth penetration profile but may reduce the absolute field intensity in the target brain region. The intensity must be such that it will enable induction of the desired physiological effect in the target neural structures in the majority of the population with stimulators available in the market. Hence the distance d—as well as other configuration parameters—must be optimized for each coil design.

2. Location of the return portions relative to the base portion. The distance between the portions must be optimized for each design: Too short a distance will lead to reduction of the total induced electric field in the target brain region, due to the effect of the return elements. Too long a distance will require long connecting coil elements and their effect must be taken into account. Furthermore, the coil size must be optimized for easy location, navigation and placement over the head.

3. Location of the return portions relative to the brain. The return elements affect closer brain regions. The location of the return portions must consider their effect on any brain structure and the design must lead to minimal undesired side effects such as motor activation or pain.

4. The type of the return elements. Return elements may be either contacting or protruding as defined above. The ratio between contacting and protruding return elements is very important in various aspects and must be optimized for each specific coil design. In general, protruding elements induce electrostatic charge accumulation on the brain surface. This leads to reduction in the absolute electric field induced in the target brain regions, and also reduction in the relative intensity of the electric field in deeper brain regions compared to superficial regions. On the other hand, contacting elements may increase the effect in adjacent brain regions. Hence a delicate optimization must be performed in each case.

5. The distance of protruding return elements from the head, in coils containing protruding return elements. Longer distance reduces the direct effect of the return elements on the brain, but increases the charge accumulation due to the presence of longer non-tangential coil elements which are connected to the return elements and move them away from the head. A delicate optimization must be performed in each case to account for this effect.

6. The overall coil inductance. The number, length, configuration and packing parameters of the coil windings must be planned to lead to coil inductance in the desired range. Usually the desired range for TMS coils inductance is between 15 and 30 microHenri. Too high inductance may reduce coil efficacy, increase pulse width and is often associated with increased coil resistance, energy consumption and coil heating. Too small inductance may lead to fast rate of change of the electric current which may damage stimulator components.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The above and further advantages of the present invention may be better understood by referring to the following description in conjunction with the accompanying drawings in which.

Figure 1:
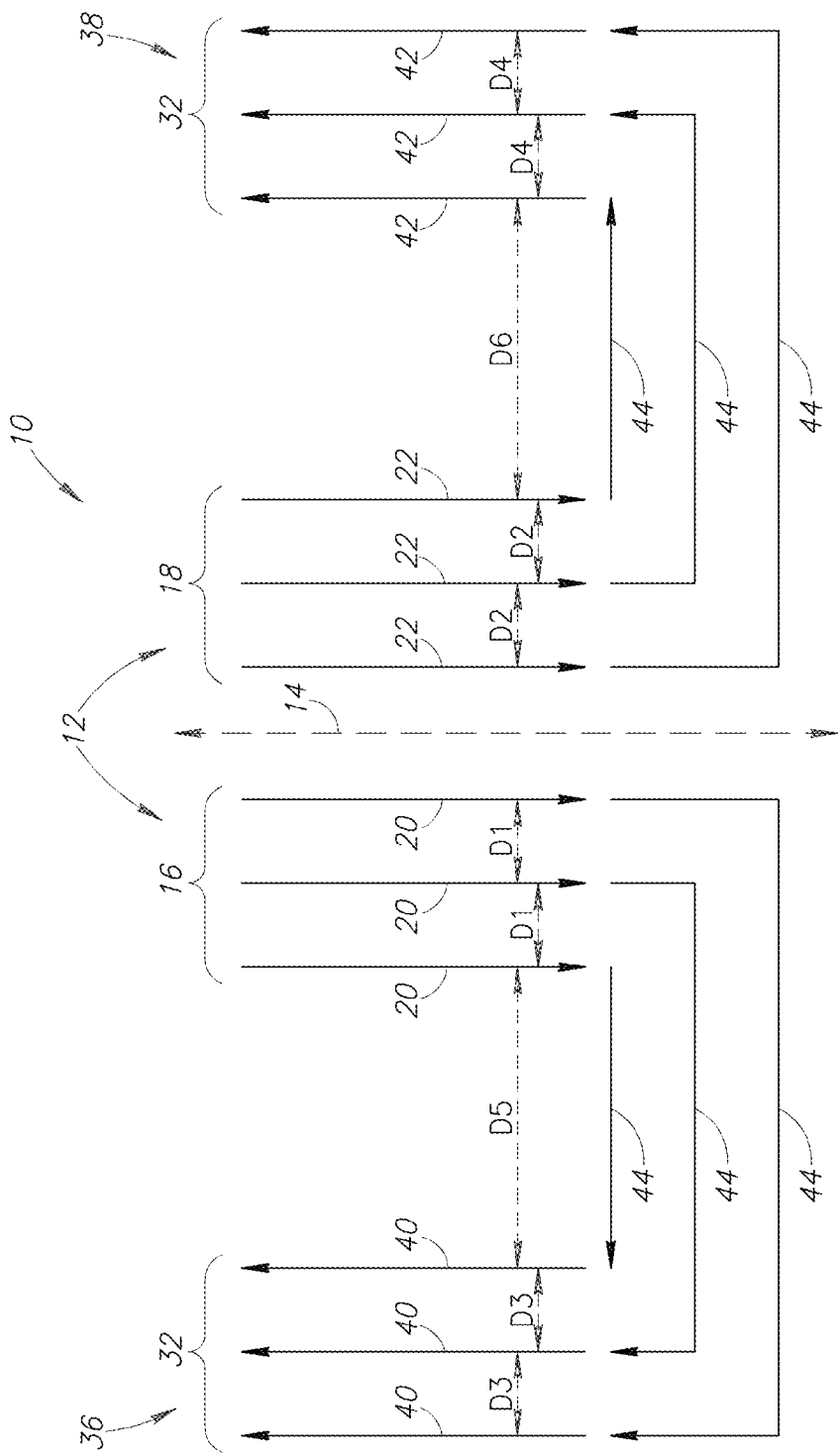
FIG. 1 is a schematic illustration showing principles of stimulation for central base coils, in accordance with embodiments of the present invention.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION OF THE INVENTION

In the following detailed description, numerous specific details are set forth in order to provide a thorough understanding of the present invention. It will be understood by those of ordinary skill in the art that the present invention may be practiced without these specific details. In other instances, well-known methods, procedures, components and structures may not have been described in detail so as not to obscure the present invention.

The present invention is directed to central base coils for deep TMS and methods of use thereof. The principles and operation of systems and methods according to the present invention may be better understood with reference to the drawings and accompanying descriptions.

Before explaining at least one embodiment of the present invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

Each of the examples below is a coil construction designed uniquely for effective activation of specific deep brain regions. Each of these coils was constructed after a complex development process including computer simulation of the electric field distribution induced in the brain by various coil configurations, building and experimenting with various prototypes, electric field measurements in a phantom head model filled with saline solution at physiologic concentration, and iterations between computer simulations and phantom brain measurements until obtaining the optimal solution for each specific target.

Reference is now made to FIG. 1, which is a schematic illustration showing principles of stimulation for central base coils, in accordance with embodiments of the present invention. In the embodiment shown in FIG. 1, a schematic illustration of a base coil depicts the elements of a central base coil in accordance with embodiments of the present invention, but does not depict the actual appearance of these elements. As shown in FIG. 1, central base coil 10 includes a base portion 12 and a return portion 32. A central axis 14 defines a midportion of coil 10. It should be readily apparent that central axis 14 may be an imaginary axis and may be straight or curved, and is used herein for descriptive purposes and for geometric orientation. Base portion 12 includes a base portion right side 16 to the right of central axis 14 and a base portion left side 18 to the left of central axis 14. Directions of right side and left side are defined in accordance with anatomical definitions. Thus, in the illustration, base portion right side 16 is on the left side of the figure and base portion left side 18 is on the right side of the figure. Base portion right side 16 includes multiple right side stimulating elements 20, depicted in FIG. 1 with arrows to illustrate the direction of electrical flow. Right side stimulating elements 20 are spaced apart from one another by distances D1. Base portion left side 18 includes multiple left side stimulating elements 22, depicted in FIG. 1 with arrows to illustrate the direction of electrical flow. The direction of electrical stimulation of left side stimulating elements 22 with respect to central axis 14 is substantially the same as the direction of electrical stimulation of right side stimulating elements 20. Left side stimulating elements 22 are spaced apart from one another by a distance D2.

Return portion 32 includes a return portion right side 36 and a return portion left side 38. Return portion right side 36 includes multiple right side return elements 40, and return portion left side 38 includes multiple left side return elements 42. Right side and left side return elements 40 and 42 are depicted in FIG. 1 with arrows to illustrate the direction of electrical flow. It should be readily apparent from FIG. 1 that the direction of electrical flow for right side and left side return elements 40 and 42 is opposite the direction of electrical flow for right side and left side stimulating elements 20 and 22, taken with respect to central axis 14. Right side return elements 40 are connected to right side stimulating elements 20 and left side return elements 42 are connected to left side stimulating elements 22 via connecting elements 44. Thus, in one embodiment, current flows through a right side return element 20 in one direction, referred to as a stimulating direction, then through a connecting element 44 in a transverse direction which is transverse to the stimulating direction, and afterwards through a return element 40 in an opposite direction which is opposite the stimulating direction and is referred to as a returning direction. In some embodiments, all or some of stimulating elements, connecting elements and return elements are comprised of a single continuous piece of coil, wherein different portions of the single piece of coil are designated as either stimulating, connecting or return elements depending on their positions and directions of current flow.

Right side return elements 40 are spaced apart from one another by a distance D3. Left side return elements 42 are spaced apart from one another by a distance D4. Right side base portion 16 and right side return portion 36 are spaced apart from one another by a distance D5. Left side base portion 18 and left side return portion 38 are spaced apart from one another by a distance D6. By having distances D5 and D6 which are sufficiently large, it is possible to minimize effects of return current on the stimulated area. In some embodiments, distances D5 and D6 are in the range of 4 to 10 cm. In other embodiments distances D5 and D6 are in the range of 6 to 8 cm. Distances D5 and D6 can be either the same or different.

Figure 2A:
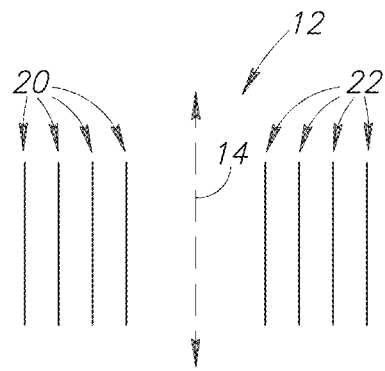
FIGS. 2A-2F are schematic illustrations of a base portion of the central base coils shown schematically in FIG. 1 in accordance with embodiments of the present invention.
Figure 2B:
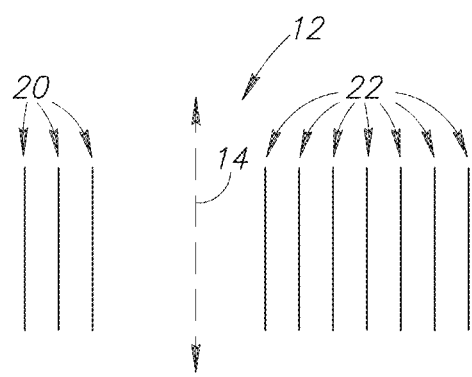
Figure 2C:
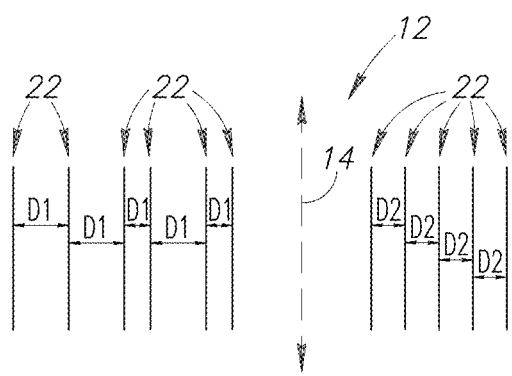
Figure 2D:
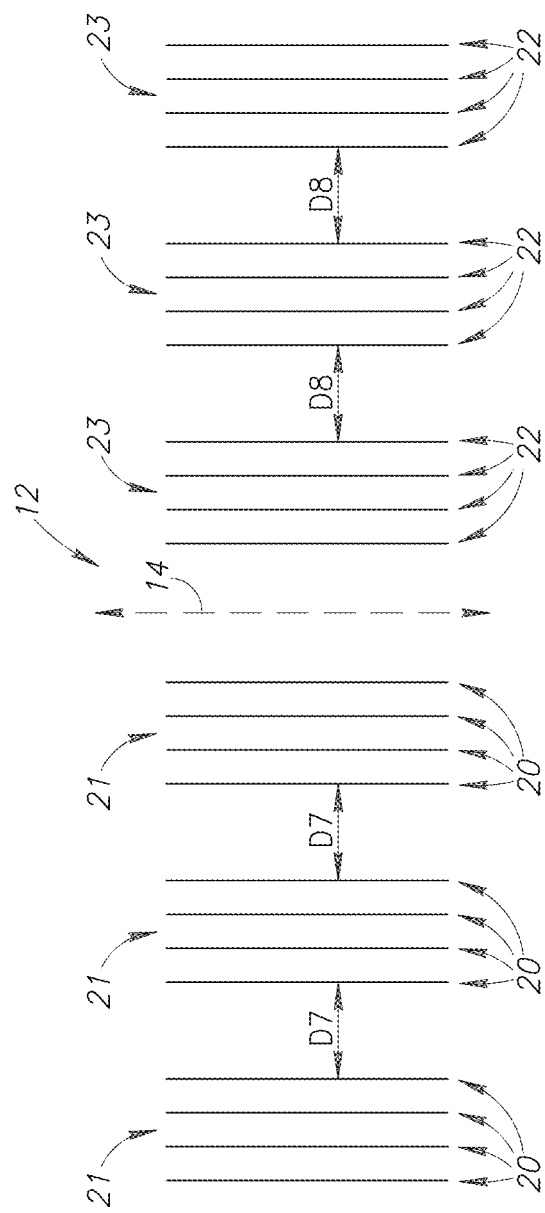
Figure 2E:
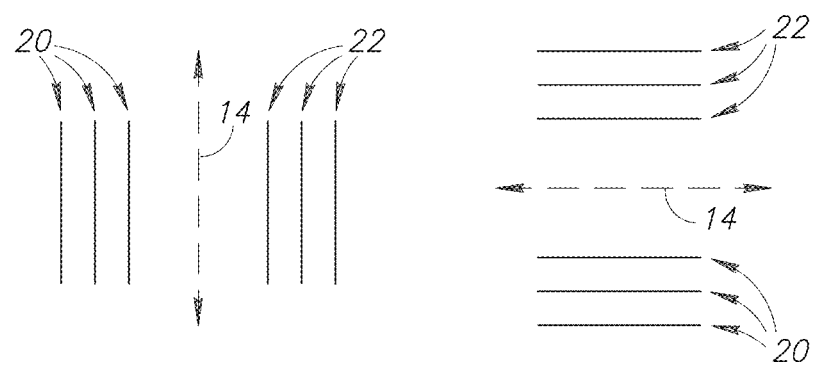
Figure 2F:
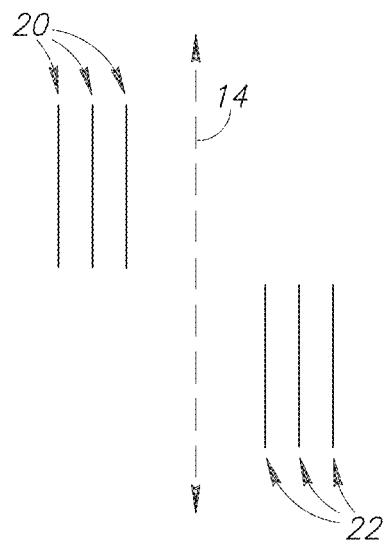

Reference is now made to FIGS. 2A-2F, which are schematic illustrations of base portion 12 in accordance with embodiments of the present invention. In some embodiments, as shown in FIG. 2A, the same number of right side stimulating elements 20 and left side stimulating elements 22 are used. In other embodiments, as shown in FIG. 2B, right side stimulating elements 20 may include a greater or lesser number of stimulating elements than left side stimulating elements 22. In some embodiments, as shown in FIG. 2C, distances D1 between right side stimulating elements 20 may be variable. In some embodiments, distances D2 between left side stimulating elements 22 may be variable. Distances D1 and/or D2 between stimulating elements may be uniform, variable or periodic. In some embodiments, distances D1 may be variable while distances D2 may be uniform, as shown in FIG. 2C, or vice versa. In some embodiments, right side and/or left side stimulating elements 20, 22 may include multiple groupings. As shown in FIG. 2D, multiple right side groupings 21 and/or multiple left side groupings 23 may be included. Distances D7, D8 between groupings may be uniform, variable or periodic. In some embodiments, as shown in FIG. 2E, multiple central axes 14 may be included, wherein each of central axes 14 may be in a different direction and includes its own base portion 12 with right side stimulating elements 20 and left side stimulating elements 22. In other embodiments, as shown in FIG. 2F, right side stimulating elements 20 are at a vertical distance from left side stimulating elements 22 with respect to central axis 14. It should be readily apparent that the embodiments shown herein are non-limiting examples of a base portion, and that other configurations may be included within the scope of the invention as well.

Figure 3:
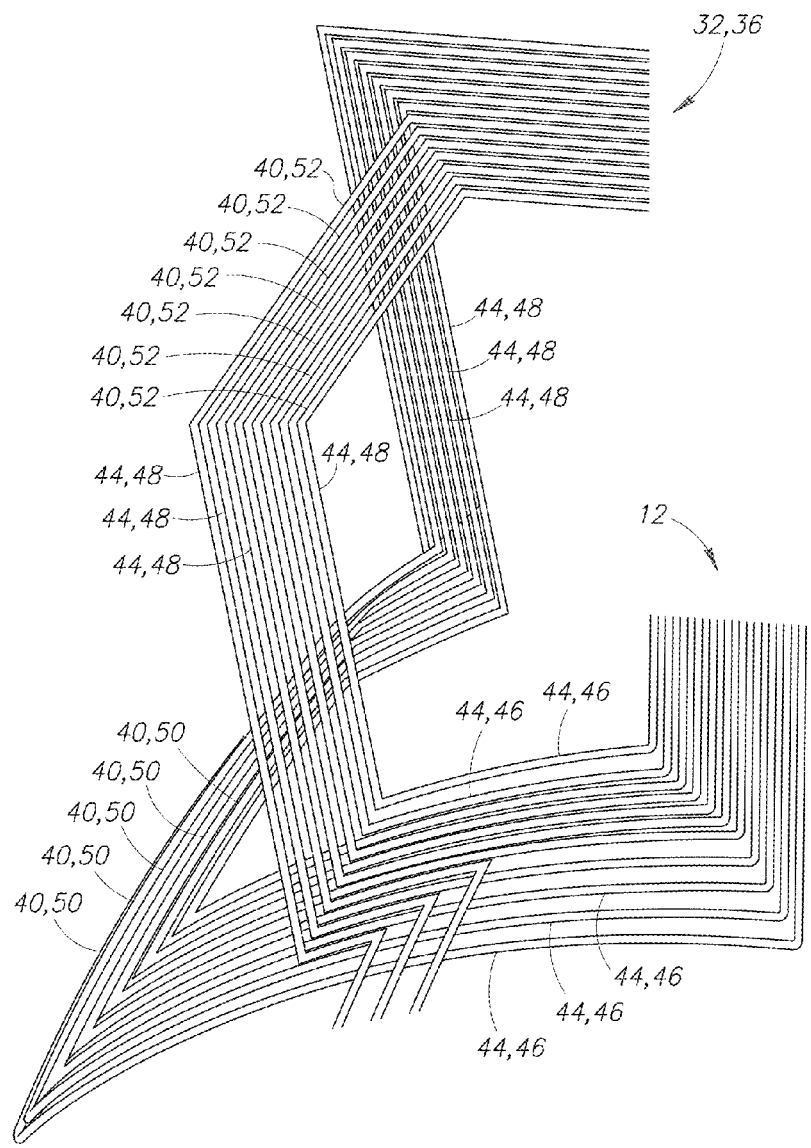
FIG. 3 is an illustration of a return portion of the central base coils shown schematically in FIG. 1, in accordance with embodiments of the present invention.

Reference is now made to FIG. 3, which is an illustration of a return portion 32, in accordance with embodiments of the present invention. Depicted in FIG. 3 is return portion right side 36, although it should be readily apparent that return portion left side may have a similar construction. Right side return elements 40 are shown at two different heights, wherein some of right side return elements 40 are configured to be in contact with a body part. These right side return elements 40 are referred to as contacting return elements 50. Some of right side return elements 40 are configured to be protruding from the body part, and are referred to as protruding return elements 52. Protruding return elements 52 may be at a vertical distance or a horizontal distance from base portion 12, as long as protruding return elements 52 are configured to protrude from coil 10 such that they are configured not to contact the body part which base portion 12 is configured to contact. Thus, connecting elements 44 may be horizontal connecting elements 46 or may be vertical connecting elements 48 or may have additional configurations as needed to connect return portion 32 to base portion 12.

In some embodiments, some of multiple right side return elements 40 are contacting return elements 50 and some of multiple right side return elements 40 are protruding return elements 52. In some embodiments, all of multiple right side return elements 40 are contacting return elements 50. In some embodiments all of multiple right side return elements 40 are protruding return elements 52. In some embodiments, some of multiple left side return elements 42 are contacting return elements 50 and some of multiple left side return elements 42 are protruding return elements 52. In some embodiments, all of multiple left side return elements 42 are contacting return elements 50. In some embodiments all of multiple left side return elements 42 are protruding return elements 52. Right side return elements 40 and left side return elements 42 may be the same type or different types from one another. For example, in some embodiments, all of right side return elements 40 are contacting return elements 50 while some of multiple left side return elements 42 are contacting return elements 50 and some of multiple left side return elements are protruding return elements 52. In other embodiments, all of right and left side return elements 40 and 42 are contacting return elements 50. Any combination of protruding and/or contacting return elements is possible and is included within the scope of the present invention.

Figure 4:
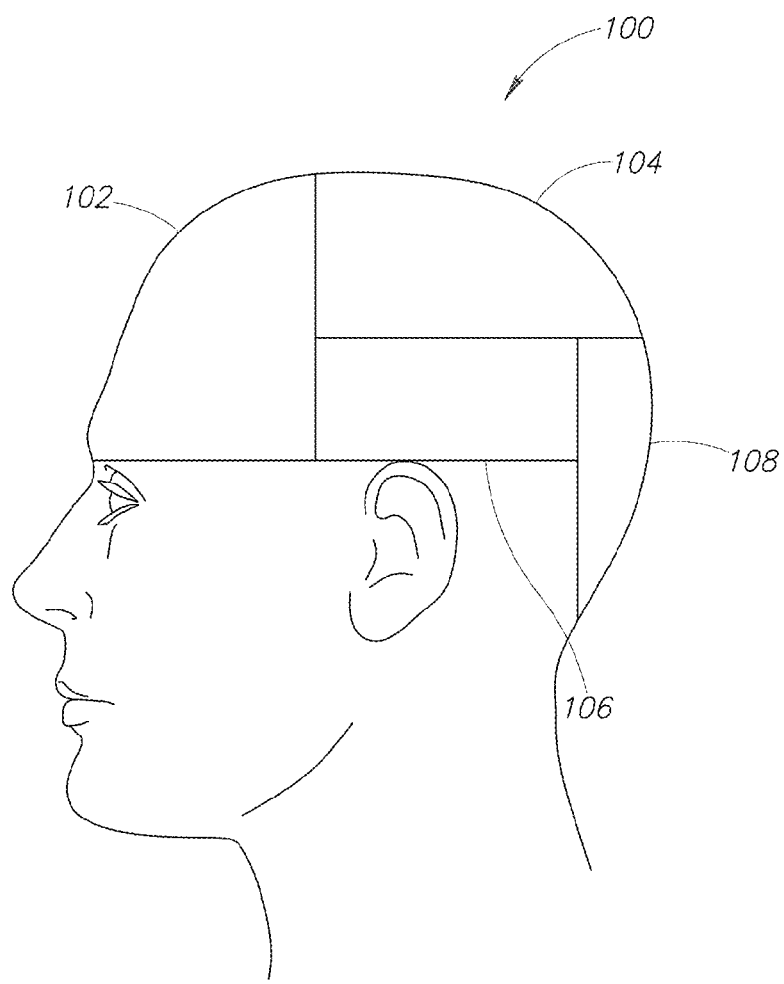
FIG. 4 is an illustration of anatomical sections of a head.

Reference is now made to FIG. 4, which is an illustration of anatomical sections of a head 100. For the purposes of illustrating the present invention, head 100 has four sections: a frontal section 102 at a front portion of head 100, a parietal section 104 to the rear of frontal section 102 and at a top portion of head 100, a temporal section 106 on the side of head 100 and an occipital section 108 at a rear portion of head 100. Central base coil 10 is configured such that central axis 14 may be positioned at a mid-point of head 100 with right side stimulating elements on one side of head 100 and left side stimulating elements on another side of head 100. In other embodiments, central axis 14 is positioned at a different location of head 100, such as a temporal section 106, and right and left side stimulating elements 20 and 22 may also be positioned on temporal section 106 or may be positioned at different locations on head 100. Thus, for example, base portion 12 may be positioned on frontal section 102, with central axis 14 running along an anterior-posterior central line. In another embodiment, base portion 12 may be positioned on temporal section 106, with central axis 14 running along a posterior-anterior central line. In yet another embodiment, base portion 12 may be positioned on parietal section 104, with central axis 14 running along a posterior-anterior central line. In yet another embodiment, base portion 12 may be positioned on frontal section 102, with central axis 14 running along a lateral-medial line. In this way, base portion 12 stimulates a section of the brain on two side of central axis 14, while return portion brings returning current back at a section which is remote from the stimulated section of the brain. In some embodiments, both base portion 12 and return portion 32 are adjacent to the head, and in some embodiments, base portion 12 is adjacent to the head while return portion 32 is remote from the head. In some embodiments base portion 12 is adjacent to the head while some of return portion 32 elements are adjacent to the head and some of return portion 32 elements are remote from the head. In some embodiments, connecting elements 44 are adjacent to the head and in other embodiments, connecting elements 44 are remote from the head. Yet in other embodiments some of connecting elements 44 are adjacent to the head and some of them are remote from the head. In some embodiments, multiple base portions 12 are used with multiple central axes, as will be described further hereinbelow.

Figure 5:
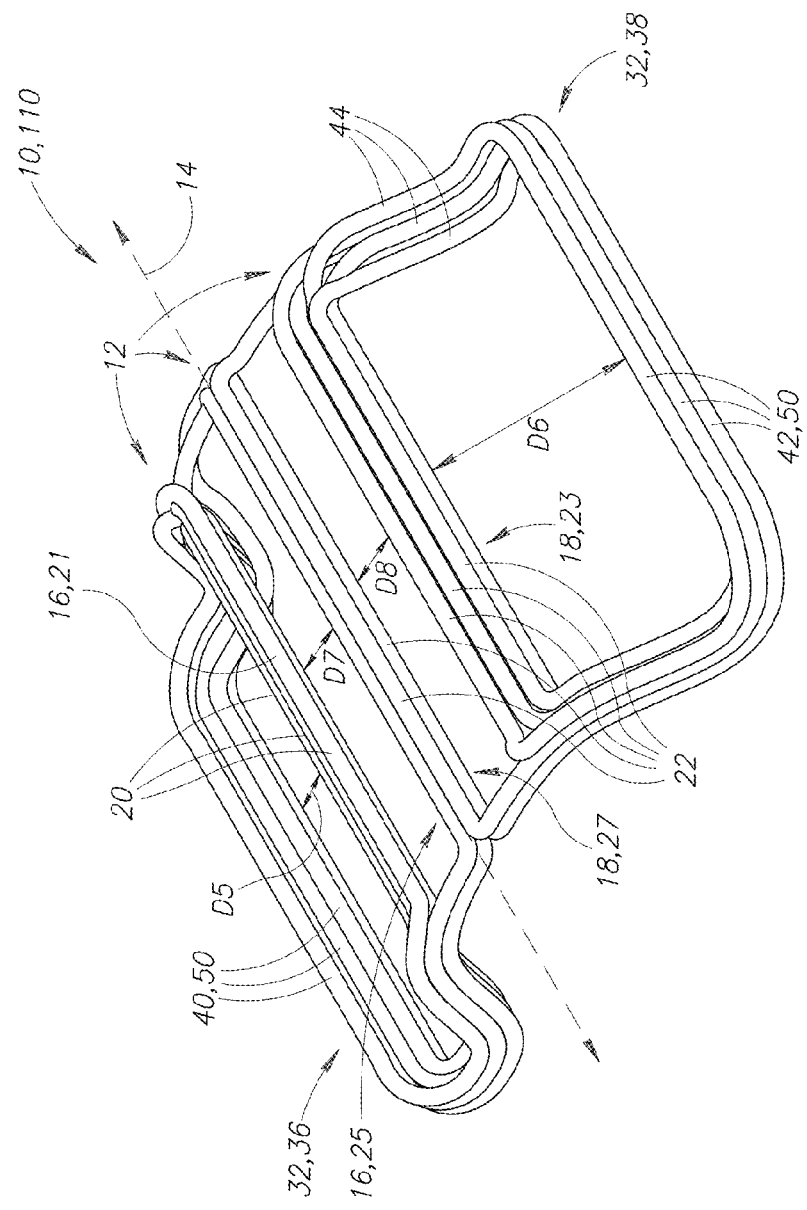
FIG. 5 is a perspective illustration of a coil, which is an example of a central base coil as shown schematically in FIG. 1, in accordance with embodiments of the present invention.

Reference is now made to FIG. 5, which is a perspective illustration of a coil 110, which is an example of a central base coil 10 in accordance with embodiments of the present invention. Coil 110 includes a base portion 12 having a base portion right side 16 and a base portion left side 18 on the two sides of central axis 14. Base portion right side 16 and base portion left side 18 are substantially horizontal and parallel with respect to central axis 14. Base portion 12 has four groupings: a first right side grouping 21, a second right side grouping 25, a first left side grouping 23, and second left side grouping 27. First and second right side groupings 21 and 25 each have right side stimulating elements 20, wherein in each of the first and second right side groupings 21 and 25, right side stimulating elements 20 are spaced relatively close to one another, with a distance D1 (not shown in the perspective illustrations due to the relatively close spacing) between right side stimulating elements 20 approximately equal to 0.3 cm. A distance D7 between first and second right side groupings 21 and 25 is approximately 2 cm. First and second left side groupings 23 and 27 each have left side stimulating elements 22, wherein in each of first and second left side groupings 23 and 27, left side stimulating elements 22 are spaced relatively close to one another, with a distance D2 between left side stimulating elements 22 approximately equal to 0.3 cm. A distance D8 between first and second left side groupings 23 and 27 is approximately 2 cm.

Coil 110 further includes a return portion 32 including a return portion right side 36 and a return portion left side 38. Return portion right side 36 includes right side return elements 40 which are contacting return elements 50 since they are configured to contact a skull when coil 110 is in place. Return portion left side 38 includes left side return elements 42 which are also contacting return elements 50.

The distance D5 between right base portion 21 and right return portion 36 is approximately 5 cm. The distance D6 between left base portion 23 and left return portion 38 is approximately 5 cm.

Coil 110 is configured to be placed on medial frontal cortex regions such as medial prefrontal cortex or medial motor cortex, and is used to stimulate medial brain regions such as the anterior cingulate cortex, and may be useful for treating, for example, blepharospasm or Tourette's syndrome.

Figure 6:
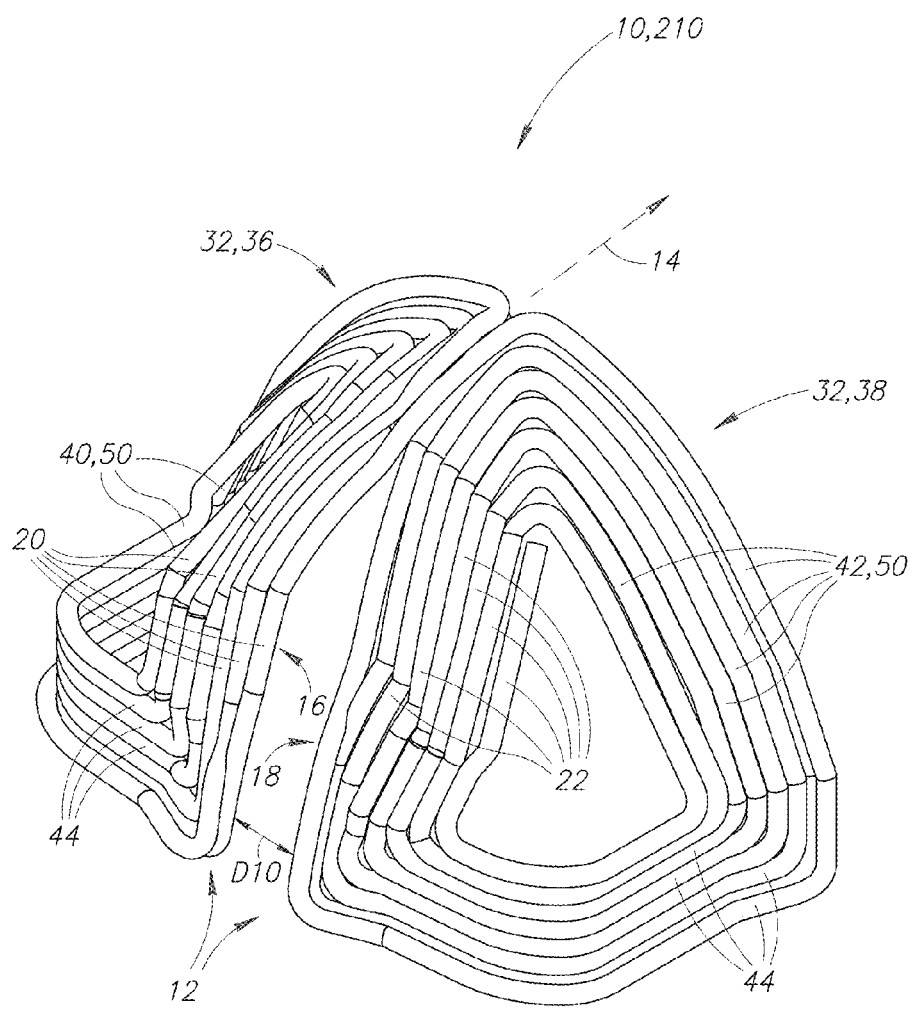
FIG. 6 is a perspective illustration of a coil, which is an example of a central base coil as shown schematically in FIG. 1, in accordance with embodiments of the present invention.

Reference is now made to FIG. 6, which is a perspective illustration of a coil 210, which is another example of a central base coil 10 in accordance with embodiments of the present invention. Coil 210 includes a base portion 12 having a base portion right side 16 and a base portion left side 18 on the two sides of central axis 14. Base portion right side 16 and base portion left side 18 are partially vertical and partially parallel with respect to central axis 14. Base portion right side 16 includes multiple right side stimulating elements 20, which are spaced apart from one another by a distance D1 of approximately 0.3 cm. Base portion left side 18 includes multiple left side stimulating elements 22, which are spaced apart from one another by a distance D2 of approximately 0.3 cm. Right side stimulating elements 20 and left side stimulating elements 22 are configured such that when coil 210 is placed on the head, the stimulating elements 20 and 22 extend from a top of the head over a portion of the forehead and/or temples. At a top portion of coil 210, base portion right side 16 and base portion left side 18 are adjacent to one another, and as the stimulating elements 20 and 22 descend, base portion right side 16 and base portion left side 18 are angled away from each other, such that at the widest point, base portion right side 16 and base portion left side 18 are a distance D10 of approximately 2 cm from one another.

Coil 210 further includes a return portion 32 including a return portion right side 36 and a return portion left side 38. Return portion right side 36 includes right side return elements 40 which are contacting return elements 50 since they are configured to contact a skull when coil 210 is in place. Return portion left side 38 includes left side return elements 42 which are also contacting return elements 50. Connecting elements 44 connect right side stimulating elements 20 to right side return elements 40 and connect left side stimulating elements 22 to left side return elements 42. Right side stimulating elements 20, connecting elements 44 and right side return elements 40 form substantially a triangular shape, and left side stimulating elements 22, connecting elements 44 and left side return elements 42 form substantially a triangular shape, wherein the triangular shape on the left side and the triangular shape on the right side are substantially in contact with one another at a top portion of coil 210.

Coil 210 is configured to be placed on medial frontal cortex regions such as medial prefrontal cortex and/or medial orbitofrontal cortex, and is used to stimulate orbitofrontal cortex regions including the paracingulate cortex, and may be useful for treating, for example, autism and Asperger's disease.

Figure 7:
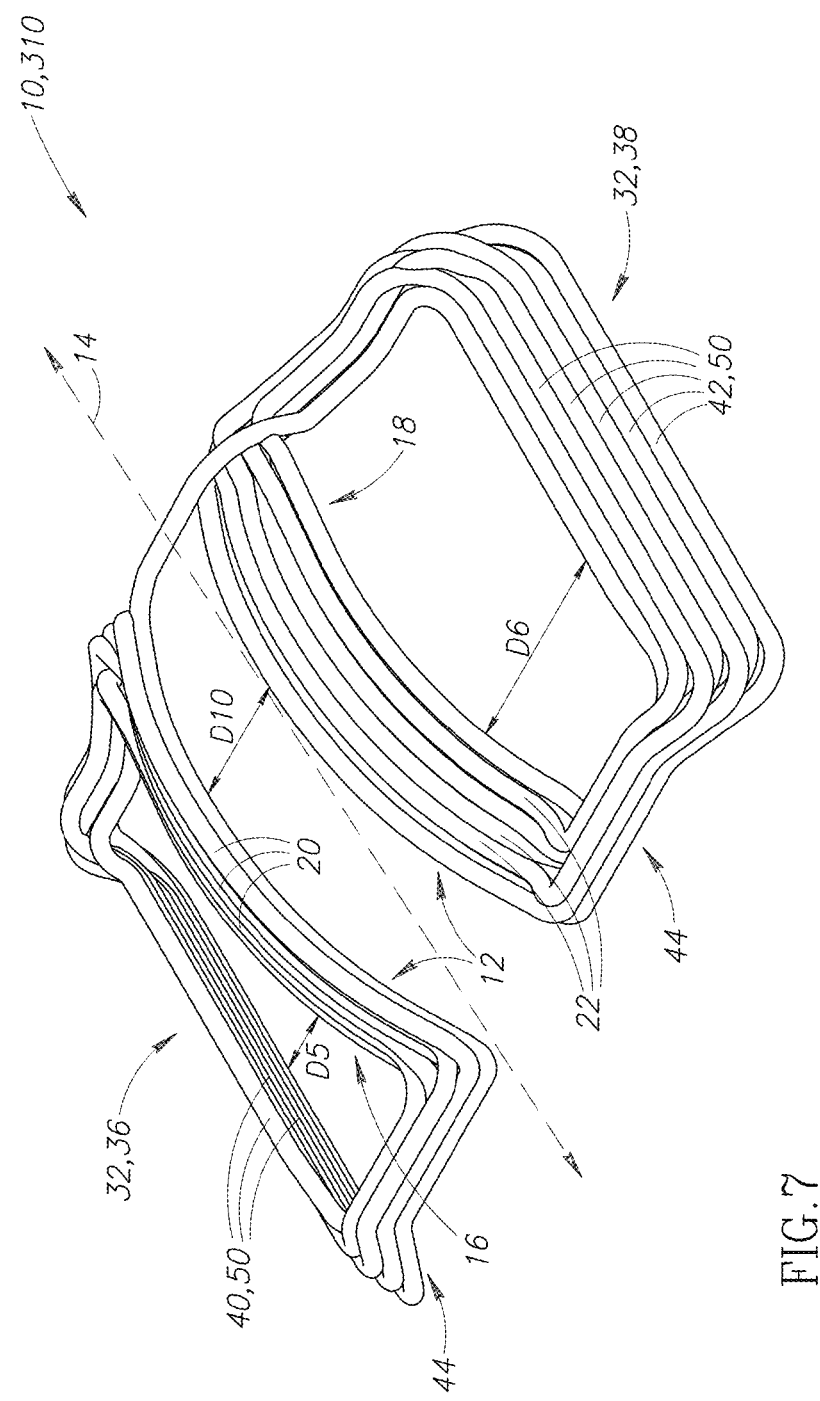
FIG. 7 is a perspective illustration of a coil, which is an example of a central base coil as shown schematically in FIG. 1, in accordance with embodiments of the present invention.

Reference is now made to FIG. 7, which is a perspective illustration of a coil 310, which is another example of a central base coil 10 in accordance with embodiments of the present invention. Coil 310 includes a base portion 12 having a base portion right side 16 and a base portion left side 18 on the two sides of central axis 14. Base portion right side 16 and base portion left side 18 are substantially horizontal and parallel to central axis 14. Base portion right side 16 includes multiple right side stimulating elements 20, which are spaced apart from one another by a distance D1 of approximately 0.3 cm. Base portion left side 18 includes multiple left side stimulating elements 22, which are spaced apart from one another by a distance D2 of approximately 0.3 cm. Right side stimulating elements 20 and left side stimulating elements 22 are configured such that when coil 310 is placed on the head, the stimulating elements 20 and 22 are in contact with the head. In one embodiment, coil 310 is positioned on top of the head with bilateral symmetry, such that stimulating elements 20 and 22 lie on top of medial head regions. In another embodiment, coil 310 is positioned on a lateral head region, such as a left or right prefrontal cortex, so that stimulating elements 20 and 22 are adjacent to lateral head regions. The distance D10 between base portion left side 18 and base portion right side 16 is approximately 4-5 cm.

Coil 310 further includes a return portion 32 including a return portion right side 36 and a return portion left side 38. Return portion right side 36 includes right side return elements 40 which are contacting return elements 50 since they are configured to contact a skull when coil 310 is in place. Return portion left side 38 includes left side return elements 42 which are also contacting return elements 50. Connecting elements 44 connect right side stimulating elements 20 to right side return elements 40 and connect left side stimulating elements 22 to left side return elements 42. In one embodiment, as shown in FIG. 7, right side stimulating elements 20, connecting elements 44 and right side return elements 40 form substantially a rectangular shape, and left side stimulating elements 22, connecting elements 44 and left side return elements 42 form substantially a rectangular shape, wherein the rectangular shape on the left side and the rectangular shape on the right side are configured to lie on a top portion of a head. In other embodiments, right side stimulating elements 20, connecting elements 44 and right side return elements 40 form other shapes, such as a substantially rectangular with angled corners, elliptical, circular shapes, or combinations thereof. Similarly, left side stimulating elements 22, connecting elements 44 and left side return elements 42 form other shapes, such as substantially rectangular with angled corners, elliptical, circular shapes, or combinations thereof.

The distance D5 between base portion right side 16 and return portion right side 36 is approximately 5 cm. The distance D6 between base portion left side 18 and return portion left side 38 is approximately 5 cm.

Coil 310 is configured to be placed on medial frontal cortex regions such as medial prefrontal cortex or medial motor cortex, or on lateral prefrontal cortex, and is used to stimulate medial and/or lateral prefrontal cortex regions, medial and/or lateral motor cortex regions, and may be useful for treating, for example, multiple sclerosis.

Figure 8:
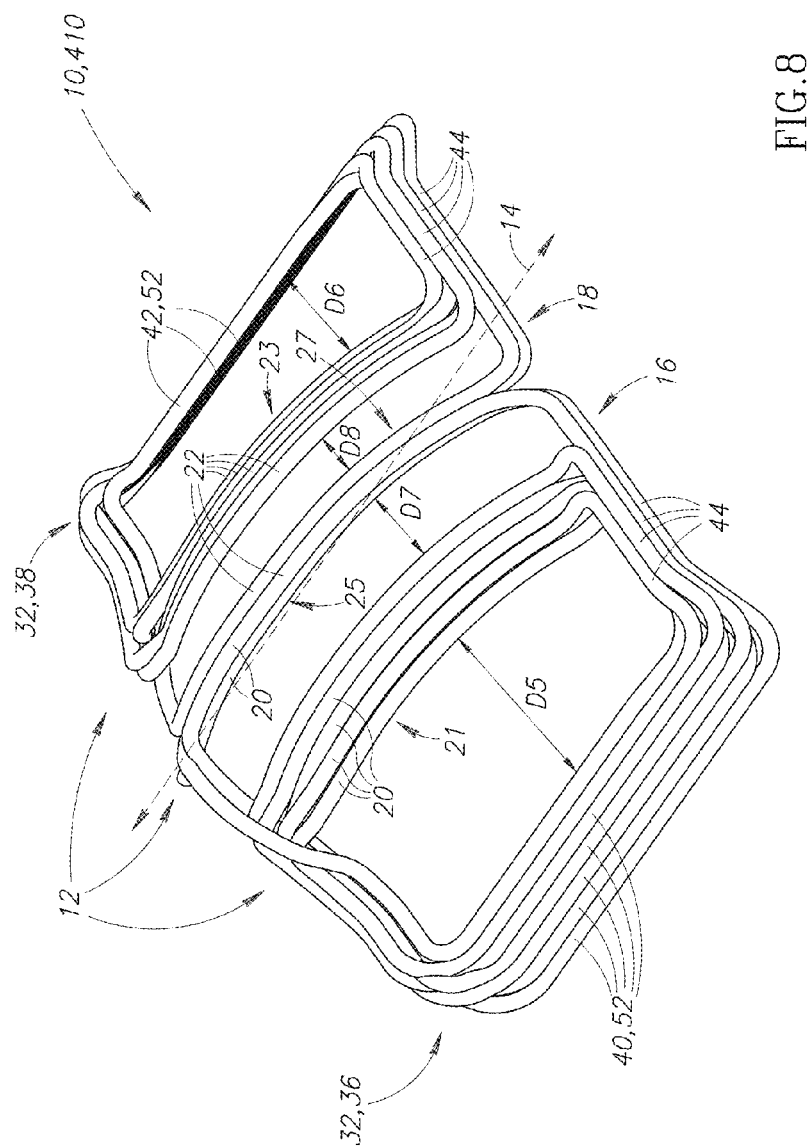
FIG. 8 is a perspective illustration of a coil, which is an example of a central base coil as shown schematically in FIG. 1, in accordance with embodiments of the present invention.

Reference is now made to FIG. 8, which is a perspective illustration of a coil 410, which is another example of a central base coil 10 in accordance with embodiments of the present invention. Coil 410 includes a base portion 12 having a base portion right side 16 and a base portion left side 18 on the two sides of central axis 14. Base portion right side 16 and base portion left side 18 are substantially horizontal and parallel to central axis 14. Base portion right side 16 includes two right side groupings 21 and 25, each of which includes multiple stimulating elements 20, which are spaced apart from one another by a distance D1 of approximately 0.3 cm. Base portion left side 18 includes two left side groupings 23 and 27, each of which includes multiple left side stimulating elements 22, which are spaced apart from one another by a distance D2 of approximately 0.3 cm. Second right side grouping 23 and second left side grouping 27 are adjacent to one another on either side of central axis 14. Right side stimulating elements 20 and left side stimulating elements 22 are configured such that when coil 410 is placed on the head, the stimulating elements 20 and 22 lie along a top of the head. The distance D7 between right side groupings 21 and 25 is approximately 2 cm. The distance D8 between left side groupings 23 and 27 is approximately 2 cm.

Coil 410 further includes a return portion 32 including a return portion right side 36 and a return portion left side 38. Return portion right side 36 includes right side return elements 40 which are protruding return elements 52 since they are configured to protrude from a skull when coil 410 is in place. Return portion left side 38 includes left side return elements 42 which are also protruding return elements 52. Connecting elements 44 connect right side stimulating elements 20 to right side return elements 40 and connect left side stimulating elements 22 to left side return elements 42. Right side stimulating elements 20, connecting elements 44 and right side return elements 40 form substantially a rectangular shape, and left side stimulating elements 22, connecting elements 44 and left side return elements 42 form substantially a rectangular shape, wherein the rectangular shape on the left side and the rectangular shape on the right side are configured to lie with base portion 12 lying on a top portion of a head and return portion 14 protruding from the head.

The distance D5 between base portion right side 16 and return portion right side 36 is approximately 5 cm. The distance D6 between base portion left side 18 and return portion left side 38 is approximately 5 cm.

Coil 410 is configured to be placed on medial frontal cortex and/or medial parietal cortex, and is used to stimulate the medial motor cortex, and may be useful for treating, for example, chronic pain or for rehabilitation of patients following stroke.

Figure 9:
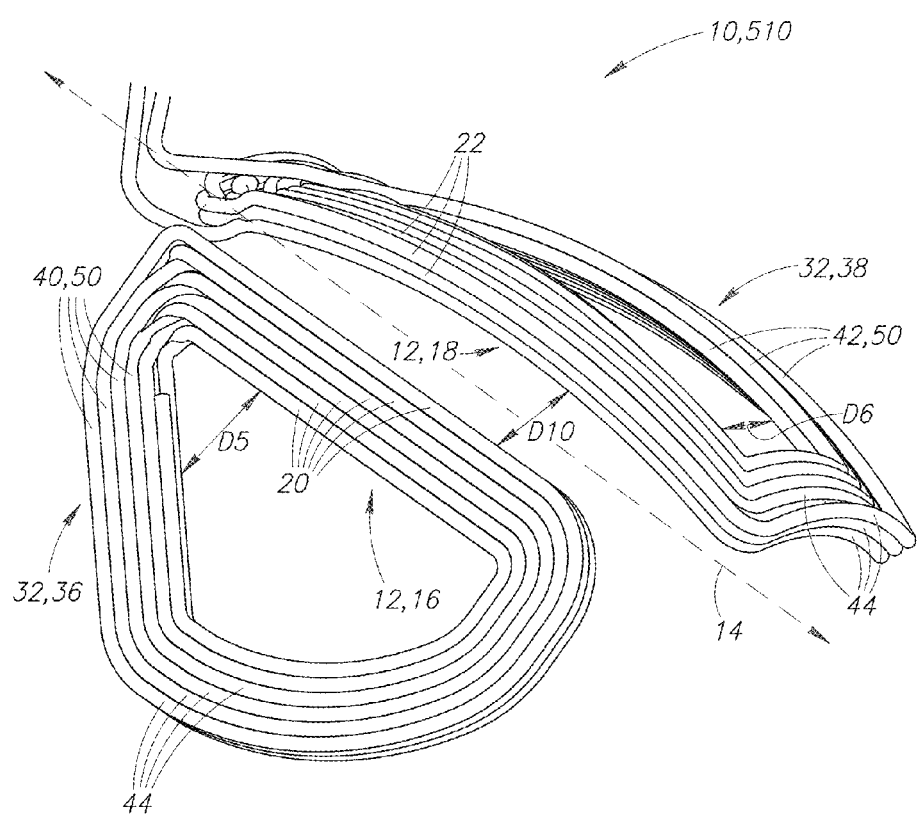
FIG. 9 is a perspective illustration of a coil, which is an example of a central base coil as shown schematically in FIG. 1, in accordance with embodiments of the present invention.

Reference is now made to FIG. 9, which is a perspective illustration of a coil 510, which is another example of a central base coil 10 in accordance with embodiments of the present invention. Coil 510 includes a base portion 12 having a base portion right side 16 and a base portion left side 18 on the two sides of central axis 14. Base portion right side 16 and base portion left side 18 are substantially horizontal with respect to central axis 14. Base portion right side 16 includes multiple right side stimulating elements 20, which are spaced apart from one another by a distance D1 of approximately 0.3 cm. Base portion left side 18 includes multiple left side stimulating elements 22, which are spaced apart from one another by a distance D2 of approximately 0.3 cm. Right side stimulating elements 20 and left side stimulating elements 22 are configured such that when coil 510 is placed on the head, the stimulating elements 20 and 22 extend over a top of the head and slightly descend down the sides of the head such that base portion right side 16 and base portion left side 18 are angled away from each other. The distance D10 between base portion left side 18 and base portion right side 16 is approximately 4-5 cm.

Coil 510 further includes a return portion 32 including a return portion right side 36 and a return portion left side 38. Return portion right side 36 includes right side return elements 40 which are contacting return elements 50 since they are configured to contact a skull when coil 510 is in place. Return portion left side 38 includes left side return elements 42 which are also contacting return elements 50. Connecting elements 44 connect right side stimulating elements 20 to right side return elements 40 and connect left side stimulating elements 22 to left side return elements 42. Right side stimulating elements 20, connecting elements 44 and right side return elements 40 form substantially a triangular shape, and left side stimulating elements 22, connecting elements 44 and left side return elements 42 form substantially a rectangular shape, wherein the rectangular shape on the left side and the triangular shape on the right side are substantially in contact with one another at a top portion of coil 510.

The distance D5 between base portion right side 16 and return portion right side 36 is approximately 5 cm. The distance D6 between base portion left side 18 and return portion left side 38 is approximately 5 cm.

Coil 510 is configured to be placed on medial frontal cortex such as medial prefrontal cortex or medial motor cortex, and is used to stimulate deep motor cortex regions at a depth of up to 3-5 cm, and may be useful for treating, for example, chronic pain, stroke rehabilitation or any motor disorder.

Figure 10:
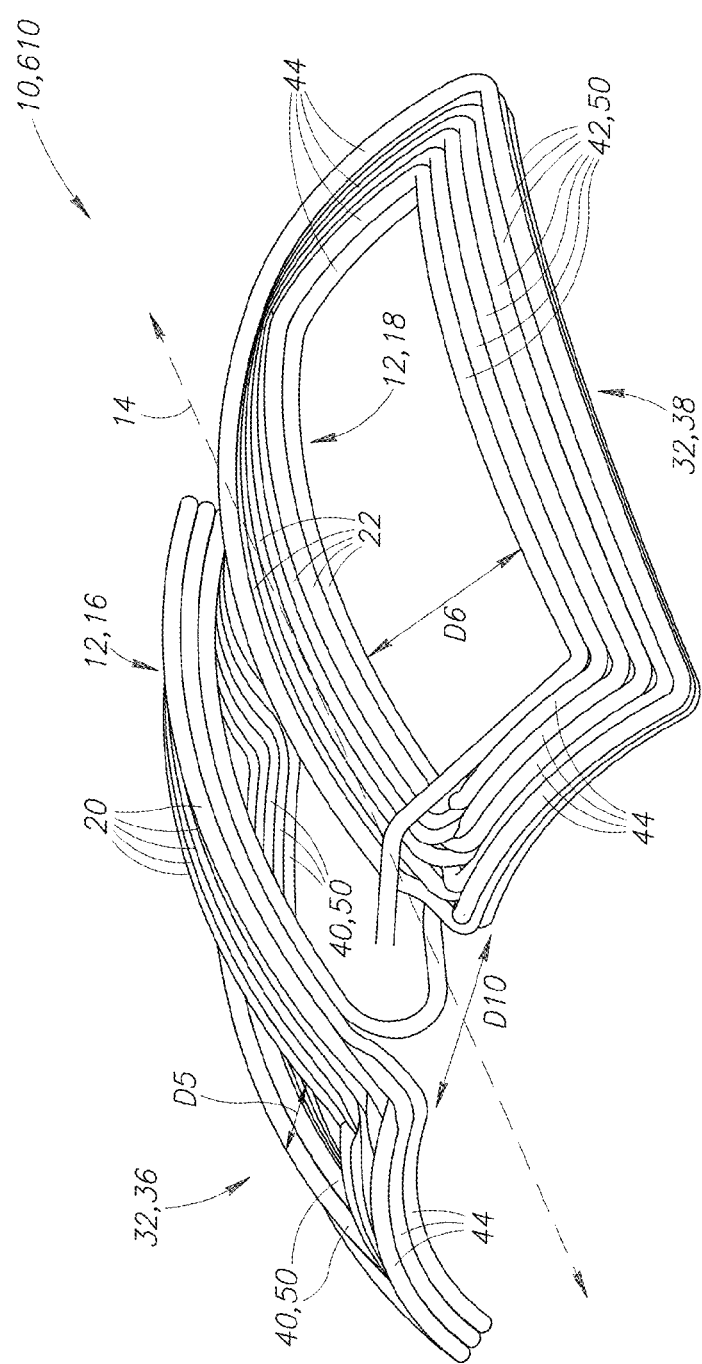
FIG. 10 is a perspective illustration of a coil, which is an example of a central base coil as shown schematically in FIG. 1, in accordance with embodiments of the present invention.

Reference is now made to FIG. 10, which is a perspective illustration of a coil 610, which is another example of a central base coil 10 in accordance with embodiments of the present invention. Coil 610 includes a base portion 12 having a base portion right side 16 and a base portion left side 18 on the two sides of central axis 14. Base portion right side 16 and base portion left side 18 are substantially horizontal and parallel to central axis 14. Base portion right side 16 includes multiple right side stimulating elements 20, which are spaced apart from one another by a distance D1 of approximately 0.3 cm. Base portion left side 18 includes multiple left side stimulating elements 22, which are spaced apart from one another by a distance D2 of approximately 0.3 cm. Right side stimulating elements 20 and left side stimulating elements 22 are configured such that when coil 610 is placed on the head, the stimulating elements 20 and 22 lie along a top of the head. The distance D10 between base portion left side 18 and base portion right side 16 is approximately 4-5 cm.

Coil 610 further includes a return portion 32 including a return portion right side 36, and a return portion left side 38. Return portion right side 36 includes right side return elements 40 which are contacting return elements 50 since they are configured to contact a skull when coil 610 is in place. Return portion left side 38 includes left side return elements 42 which are also contacting return elements 50. Connecting elements 44 connect right side stimulating elements 20 to right side return elements 40 and connect left side stimulating elements 22 to left side return elements 42. Right side stimulating elements 20, connecting elements 44 and right side return elements 40 form substantially a rectangular shape, and left side stimulating elements 22, connecting elements 44 and left side return elements 42 form substantially a rectangular shape, wherein the rectangular shape on the left side and the rectangular shape on the right side are configured to lie on a top portion of a head.

The distance D5 between base portion right side 16 and return portion right side 36 is approximately 5 cm. The distance D6 between base portion left side 18 and return portion left side 38 is approximately 5 cm.

Coil 610 is configured to be placed on medial frontal cortex regions such as medial prefrontal cortex or medial motor cortex, and is used to stimulate motor cortex regions, and may be useful for treating, for example, chronic pain, stroke rehabilitation, or any motor disorder.

Figure 11:
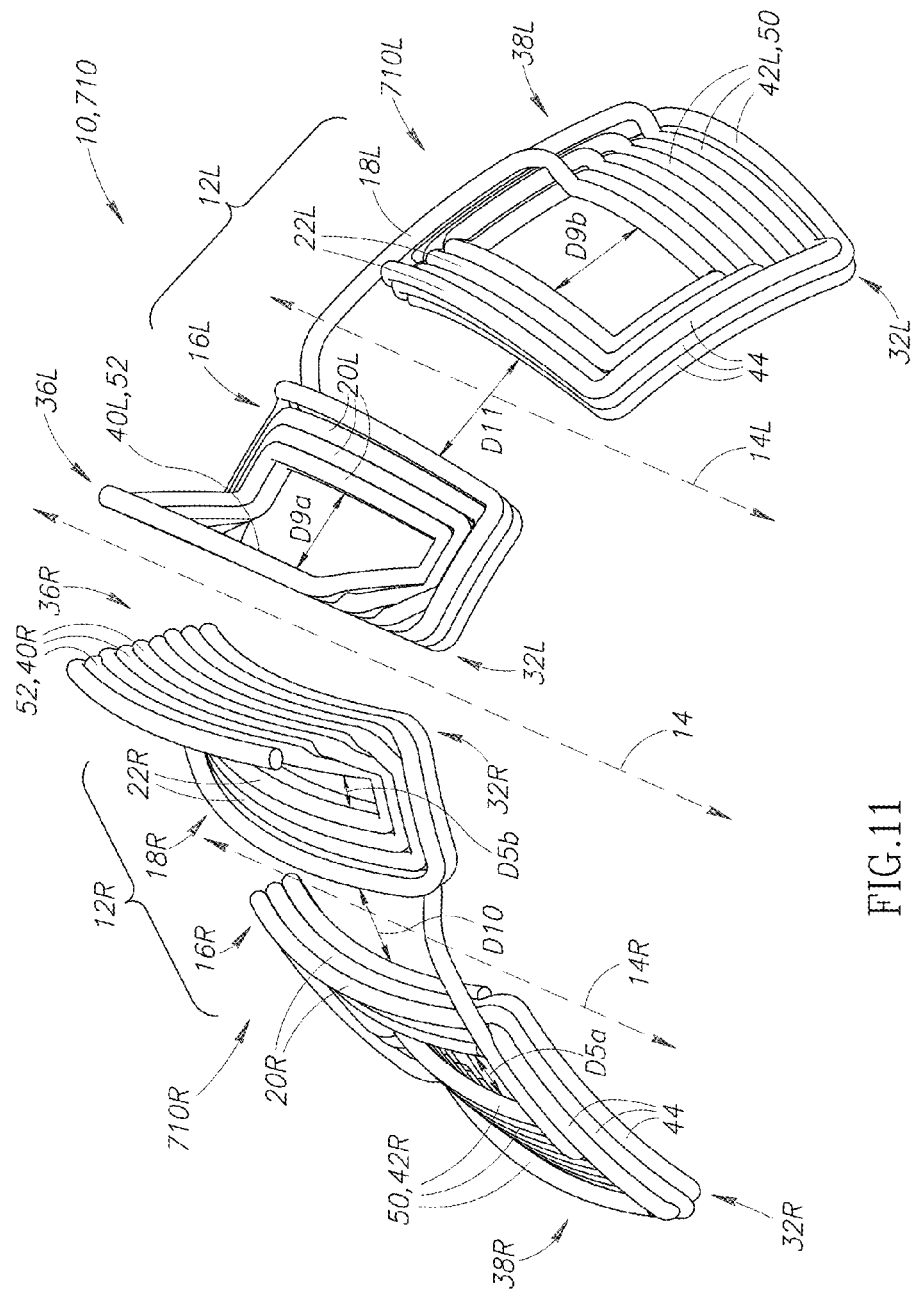
FIG. 11 is a perspective illustration of a coil, which is an example of a central base coil as shown schematically in FIG. 1, in accordance with embodiments of the present invention.

Reference is now made to FIG. 11, which is a perspective illustration of a coil 710, which is another example of a central base coil 10 in accordance with embodiments of the present invention. Coil 710 is a combination coil, which is comprised of two separate coils positioned together within a single helmet. A central axis 14 separates the two coils from one another. A first coil 710R, is positioned on a right side of central axis 14 and a second coil 710L is positioned on a left side of central axis 14. First coil 710R includes a first coil base portion 12R having a first coil base portion right side 16R and a first coil base portion left side 18R on the two sides of a first coil central axis 14R. Second coil 710L includes a second coil base portion 12L having a second coil base portion right side 16L and a second coil base portion left side 18L on the two sides of a second coil central axis 14L. First coil base portion right side 16R and first coil base portion left side 18R are substantially horizontal and parallel to first coil central axis 14R. Second coil base portion right side 16L and second coil base portion left side 18L are substantially horizontal and parallel to second coil central axis 14L. First coil base portion right side 16R includes multiple first coil outer section stimulating elements 20R, which are spaced apart from one another by a distance D1 of approximately 0.3 cm. First coil base portion left side 18R includes multiple first coil inner portion stimulating elements 22R, which are spaced apart from one another by a distance D2 of approximately 0.3 cm. Second coil base portion right side 16L includes multiple second coil inner portion stimulating elements 20L, which are spaced apart from one another by a distance D1 of approximately 0.3 cm. Second coil base portion left side 18L includes multiple second coil outer portion stimulating elements 22L, which are spaced apart from one another by a distance D2 of approximately 0.3 cm. Coil 710 is configured such that when placed on the head, the stimulating elements 20R, 20L, 22R and 22L lie along the sides of the head. The distance D10 between first coil base portion left side 18R and first coil base portion right side 16R is approximately 2 cm. The distance D11 between second coil base portion left side 18L and second coil base portion right side 16L is approximately 2 cm.

First coil 710R further includes a first coil return portion 32R including a first coil return portion inner section 36R and a first coil return portion outer section 38R. First coil return portion inner section 36R includes first coil inner section return elements 40R, which are protruding return elements 52 since they are configured to protrude vertically from a skull when coil 710 is in place. In some embodiments, first coil inner section return elements 40R are configured such that a first return element is configured to contact a skull, a second return element is positioned directly above the first return element, and so on, until all of the first coil inner section return elements form a vertically protruding column of return elements. First coil return portion outer section 38R includes first coil outer section return elements 42R, which are contacting return elements 50. Similarly, second coil 710L further includes a second coil return portion 32L including a second coil return portion inner section 36L and a second coil return portion outer section 38L. Second coil return portion inner section 36L includes second coil inner section return elements 40L, which are protruding return elements 52 since they are configured to protrude vertically from a skull when coil 710 is in place. In some embodiments, second coil inner section return elements 40L are configured such that a first return element is configured to contact a skull, a second return element is positioned directly above the first return element, and so on, until all of the first coil inner section return elements form a vertically protruding column of return elements. Second coil return portion outer section 38L includes second coil outer section return elements 42L, which are contacting return elements 50. Connecting elements 44 connect first coil right side stimulating elements 20R to first coil inner section return elements 40R, connect first coil left side stimulating elements 22R to first coil outer section return elements 42R, connect second coil right side stimulating elements 20L to second coil inner section return elements 40L, and connect second coil left side stimulating elements 22L to second coil outer section return elements 42L. First coil right side stimulating elements 20R, connecting elements 44 and first coil inner section return elements 40R form substantially a rectangular shape, first coil left side stimulating elements 22R, connecting elements 44 and first coil outer section return elements 42R form substantially a rectangular shape, wherein the rectangular shape on the left side and the rectangular shape on the right side of first coil 710R are configured to lie on a right side of a head. Second coil right side stimulating elements 20L, connecting elements 44 and second coil inner section return elements 40L form substantially a rectangular shape, second coil left side stimulating elements 22L, connecting elements 44 and second coil outer section return elements 42L form substantially a rectangular shape, wherein the rectangular shape on the left side and the rectangular shape on the right side of second coil 710L are configured to lie on a left side of a head.

The distance D5a between first coil base portion right side 16R and first coil return portion outer section 38R is approximately 2.5 cm. The distance D5b between first coil base portion left side 18R and first coil return portion inner section 36R is approximately 2.5 cm. The distance D9a between second coil base portion right side 16L and second coil return portion inner section 36L is approximately 2.5 cm. The distance D9b between second coil base portion left side 18L and second coil return portion outer section 38L is approximately 2.5 cm.

Coil 710 is configured to be placed on medial or lateral frontal cortex regions such as medial or lateral prefrontal cortex, and is used to stimulate prefrontal cortex regions, and may be useful for treating, for example, multiple sclerosis, or attention deficit and hyperactivity disorder (ADHD), or major depression.

Figure 12:
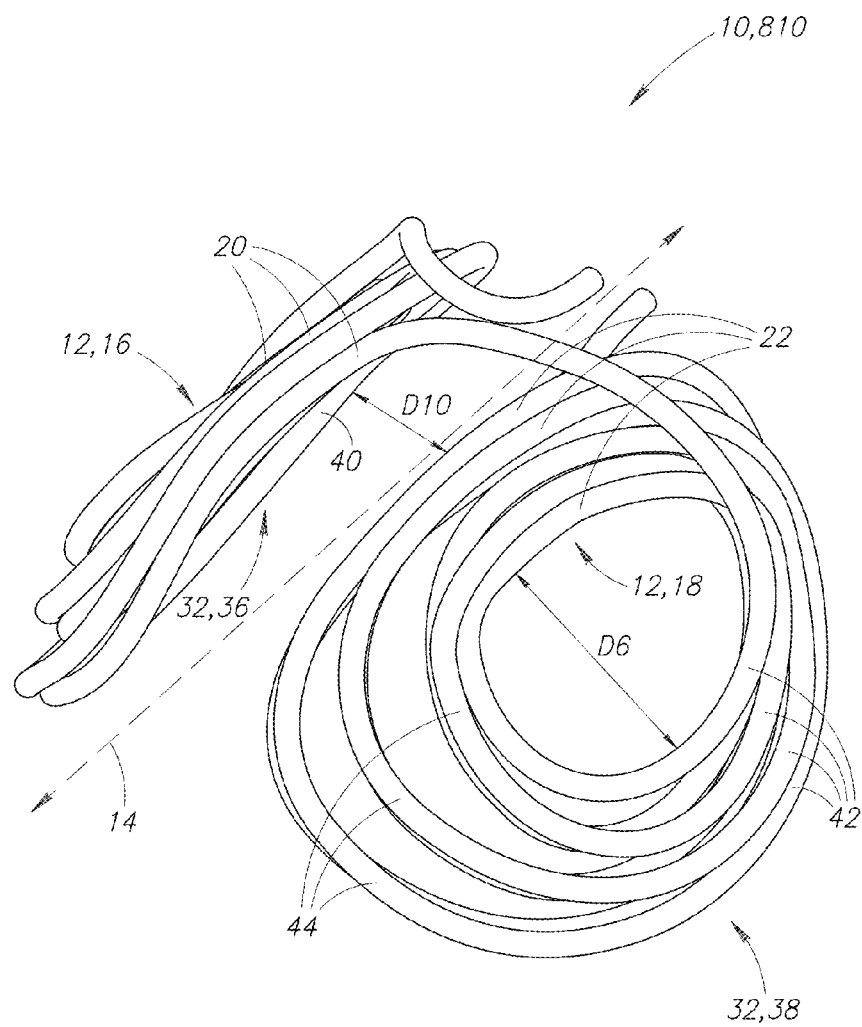
FIG. 12 is a perspective illustration of a coil, which is an example of a central base coil as shown schematically in FIG. 1, in accordance with embodiments of the present invention.

Reference is now made to FIG. 12, which is a perspective illustration of a coil 810, which is another example of a central base coil 10 in accordance with embodiments of the present invention. Coil 810 includes a base portion 12 having a base portion right side 16 and a base portion left side 18 on the two sides of central axis 14. Base portion right side 16 and base portion left side 18 are substantially horizontal and parallel to central axis 14. Base portion right side 16 includes multiple right side stimulating elements 20, which are spaced apart from one another by a distance D1 of approximately 0.3 cm. Base portion left side 18 includes multiple left side stimulating elements 22, which are spaced apart from one another by a distance D2 of approximately 0.3 cm. Right side stimulating elements 20 and left side stimulating elements 22 are configured such that when coil 810 is placed on the head, the stimulating elements 20 and 22 lie along a top of a medial portion of the head. The distance D10 between base portion left side 18 and base portion right side 16 is between 2 and 5 cm.

Coil 810 further includes a return portion 32 including a return portion right side 36 and a return portion left side 38. Return portion right side 36 includes right side return elements 40 which are contacting return elements 50 since they are configured to contact a skull when coil 810 is in place. Return portion left side 38 includes left side return elements 42 which are also contacting return elements 50. Connecting elements 44 connect right side stimulating elements 20 to right side return elements 40 and connect left side stimulating elements 22 to left side return elements 42. Connecting elements 44 and right and left side return elements 40 and 42 are curved such that right side stimulating elements 20, connecting elements 44 and right side return elements 40 form substantially a circular shape, and left side stimulating elements 22, connecting elements 44 and left side return elements 42 form substantially a circular shape. Each of the circular shapes are configured to lie on a top and side portion of a head.

The distance D5 (not shown due to the angle of the figure) between base portion right side 16 and return portion right side 36 is approximately 5 cm. The distance D6 between base portion left side 18 and return portion left side 38 is approximately 5 cm.

Coil 810 is configured to be placed on medial frontal cortex regions such as medial prefrontal cortex or medial motor cortex, and is used to stimulate the anterior cingulate cortex, and may be useful for treating, for example, mood disorders including major depressive disorder, drug addiction or other types of addiction, obsessive-compulsive disorder (OCD), chronic pain, Tourette's syndrome, or blepharospasm.

Figure 13A:
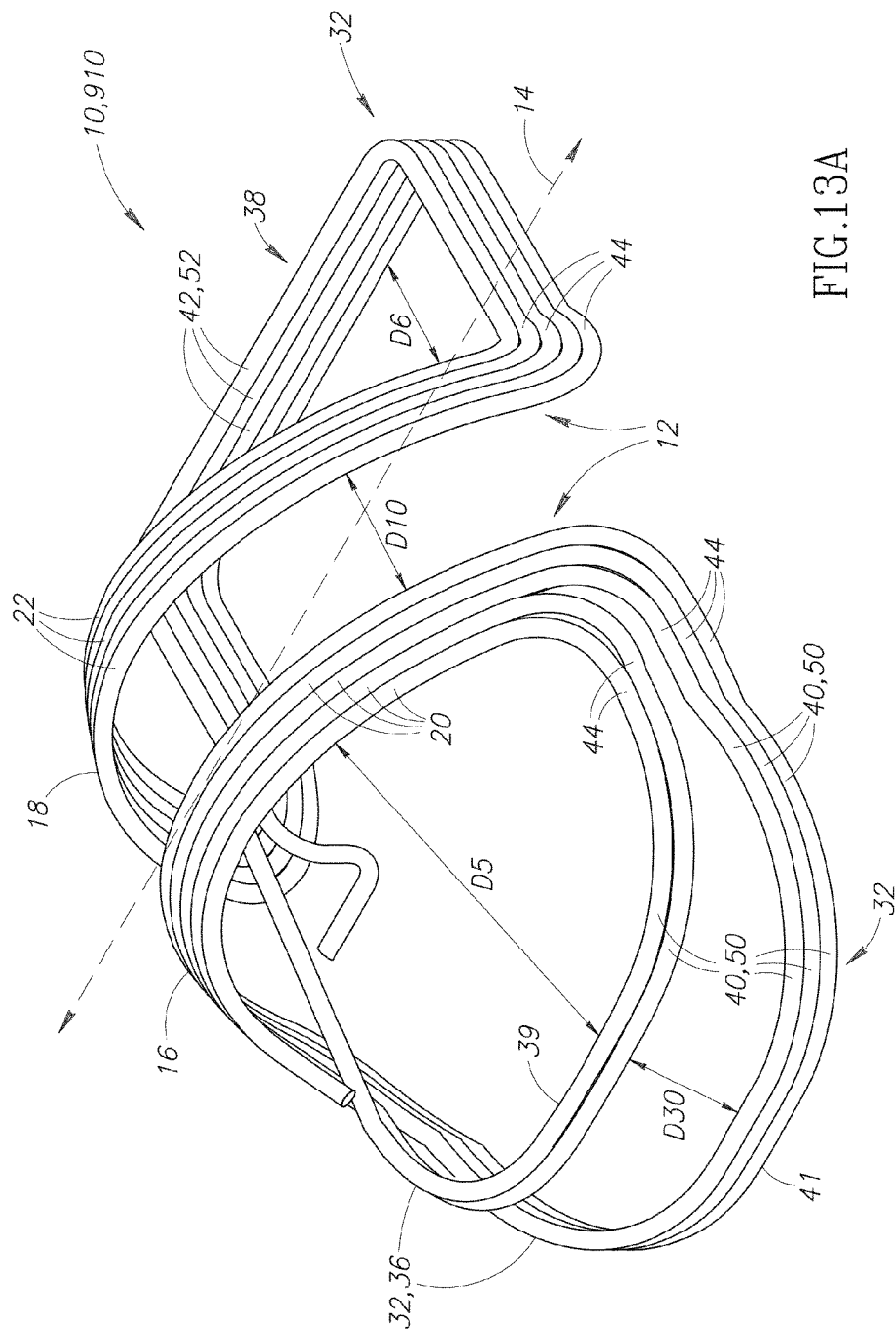
FIGS. 13A and 13B are perspective illustrations of a coil, shown off and on a head, respectively, which is an example of a central base coil as shown schematically in FIG. 1, in accordance with embodiments of the present invention.
Figure 13B:
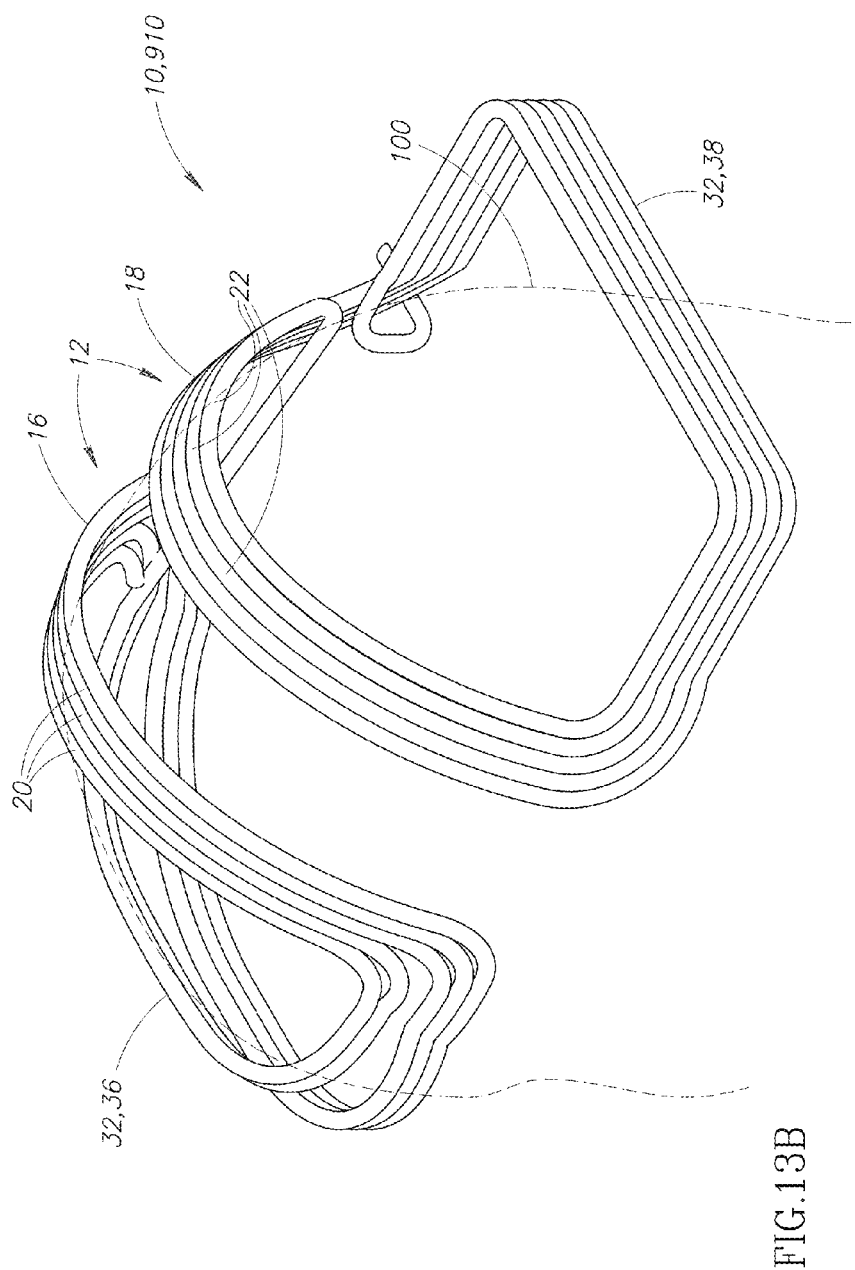

Reference is now made to FIGS. 13A and 13B, which are perspective illustrations of a coil 910, showing details of coil 910 and positioning of coil 910 on a head, respectively. Coil 910 is another example of a central base coil 10 in accordance with embodiments of the present invention. Coil 910 includes a base portion 12 having a base portion right side 16 and a base portion left side 18 on the two sides of central axis 14. For this embodiment, central axis 14 runs in a lateral/medial direction, such that when coil 910 is positioned on a skull, base portion right side 16 lies in front of base portion left side. Base portion right side 16 and base portion left side 18 are substantially horizontal and parallel to central axis 14 and are curved to conform to a shape of the skull. Base portion right side 16 includes multiple right side stimulating elements 20, which are spaced apart from one another by a distance D1 of approximately 0.3 cm. Base portion left side 18 includes multiple left side stimulating elements 22, which are spaced apart from one another by a distance D2 of approximately 0.3 cm. Right side stimulating elements 20 and left side stimulating elements 22 are configured such that when coil 810 is placed on the head, the stimulating elements 20 and 22 lie along a top of a lateral/medial portion of the head. The distance D10 between base portion left side 18 and base portion right side 16 is between 4 and 7 cm.

Coil 910 further includes a return portion 32 including a return portion right side 36 and a return portion left side 38. Return portion right side 36 includes an upper right side return portion 39 and a lower right side return portion 41. Upper right side return portion 39 and lower right side return portion 41 are separated from one another by a distance D30 of 2-3 cm. Right side return elements 40 are contacting return elements 50 since they are configured to contact a skull when coil 910 is in place. In the embodiment shown herein, right side return elements 40 are configured to contact an anterior portion of the head (i.e., the forehead), and are at least partially curved to conform to the anatomy of the anterior portion of the head. Return portion left side 38 includes left side return elements 42 which are protruding return elements 52, wherein left side return elements 42 protrude from a posterior portion of the skull. In the embodiment shown herein, left side return elements 42 are substantially straight, although other configurations are possible as well. Connecting elements 44 connect right side stimulating elements 20 to right side return elements 40 and connect left side stimulating elements 22 to left side return elements 42.

The distance D5 between base portion right side 16 and return portion right side 36 is approximately 10 cm. The distance D6 between base portion left side 18 and return portion left side 38 is approximately 10 cm.

Coil 910 is configured to be placed on medial frontal cortex or medial parietal cortex, and is used to stimulate the posterior cingulate cortex and other parietal cortex regions, and may be useful for treating, for example, mild cognitive impairment (MCI) and Alzheimer's disease.

Figure 14:
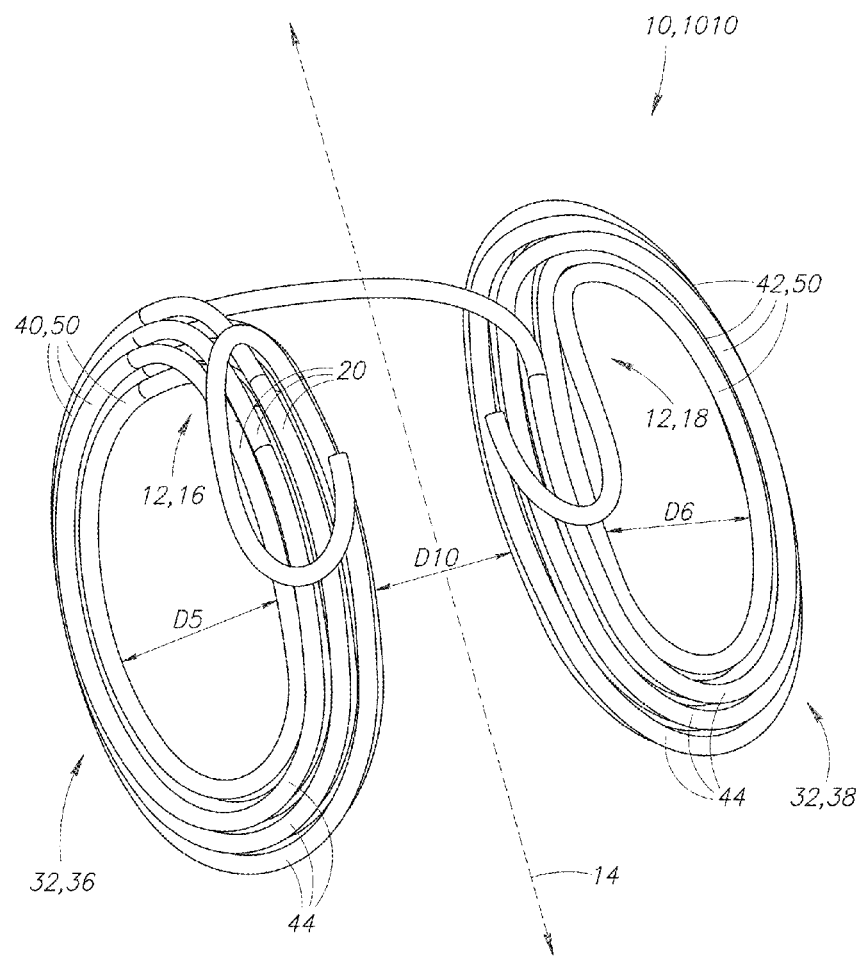
FIG. 14 is a perspective illustration of a coil, which is an example of a central base coil as shown schematically in FIG. 1, in accordance with embodiments of the present invention.

Reference is now made to FIG. 14, which is a perspective illustration of a coil 1010, in accordance with yet additional embodiments of the present invention.

Coil 1010 includes a base portion 12 having a base portion right side 16 and a base portion left side 18 on the two sides of central axis 14. Base portion right side 16 and base portion left side 18 are substantially horizontal and parallel to central axis 14. Base portion right side 16 includes multiple right side stimulating elements 20, which are spaced apart from one another by a distance D1 of approximately 0.3 cm. Base portion left side 18 includes multiple left side stimulating elements 22, which are spaced apart from one another by a distance D2 of approximately 0.3 cm. Right side stimulating elements 20 and left side stimulating elements 22 are configured such that when coil 1010 is placed on the head, the stimulating elements 20 and 22 lie along a top of a medial portion of the head. The distance D10 between base portion left side 18 and base portion right side 16 is between 4 and 8 cm.

Coil 1010 further includes a return portion 32 including a return portion right side 36 and a return portion left side 38. Return portion right side 36 includes right side return elements 40 which are contacting return elements 50 since they are configured to contact a skull when coil 1010 is in place. Return portion left side 38 includes left side return elements 42 which are also contacting return elements 50. Connecting elements 44 connect right side stimulating elements 20 to right side return elements 40 and connect left side stimulating elements 22 to left side return elements 42. Connecting elements 44 and right and left side return elements 40 and 42 are curved such that right side stimulating elements 20, connecting elements 44 and right side return elements 40 form substantially a circular shape, and left side stimulating elements 22, connecting elements 44 and left side return elements 42 form substantially a circular shape. Each of the circular shapes are configured to lie on a top and side portion of a head.

The distance D5 between base portion right side 16 and return portion right side 36 is approximately 6 cm. The distance D6 between base portion left side 18 and return portion left side 38 is approximately 6 cm.

Coil 1010 is configured to be placed on medial frontal cortex regions such as medial prefrontal cortex or medial motor cortex, and is used to stimulate the medial cortex regions including motor cortex regions, and may be useful for treating, for example, chronic pain and rehabilitation following stroke.

Figure 15:
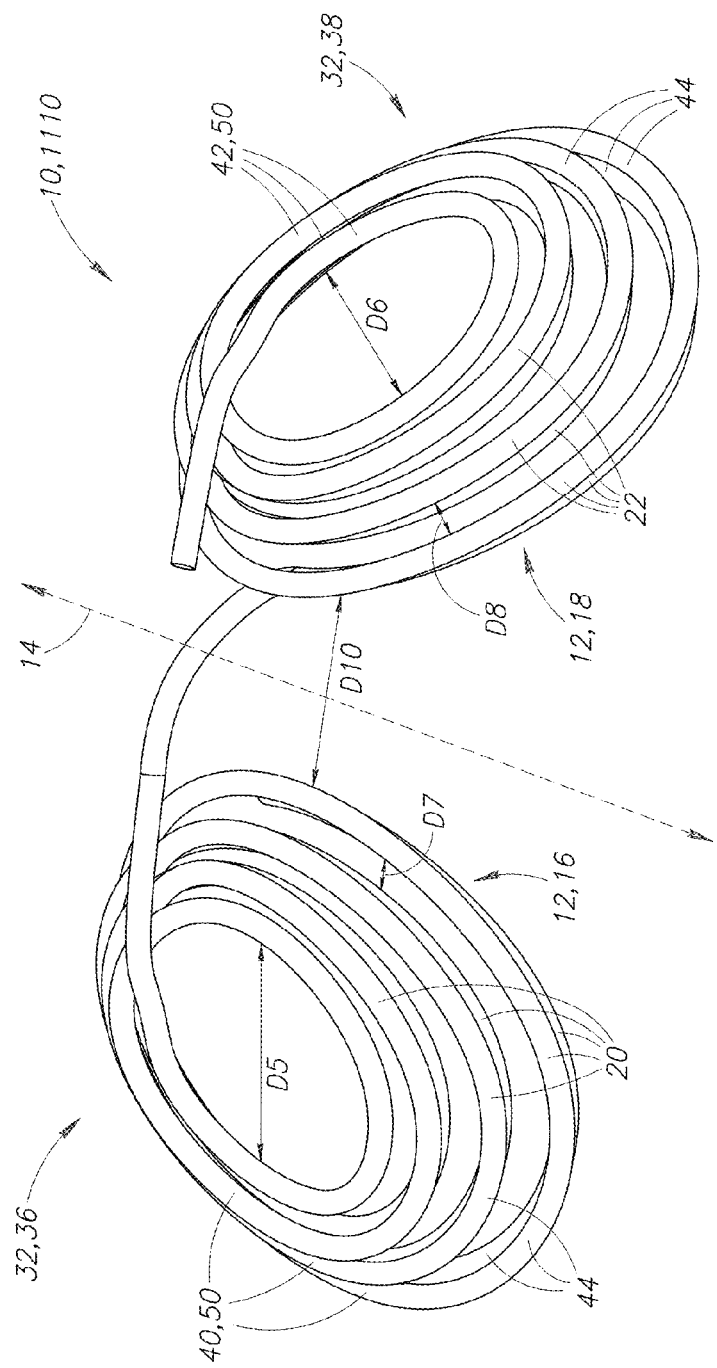
FIG. 15 is a perspective illustration of a coil, which is an example of a central base coil as shown schematically in FIG. 1, in accordance with embodiments of the present invention.

Reference is now made to FIG. 15, which is a perspective illustration of a coil 1110, in accordance with additional embodiments of the present invention.

Coil 1110 includes a base portion 12 having a base portion right side 16 and a base portion left side 18 on the two sides of central axis 14. Base portion right side 16 and base portion left side 18 are substantially curved with respect to central axis 14. Base portion right side 16 includes multiple right side stimulating elements 20, which are spaced apart from one another by a distance D1 of approximately 0.3 cm. Base portion left side 18 includes multiple left side stimulating elements 22, which are spaced apart from one another by a distance D2 of approximately 0.3 cm. In some embodiments, stimulating elements 22 are grouped in pairs, wherein each pair of stimulating elements 22 is spaced apart from another pair of stimulating elements 22 by a distance D8 of approximately 1 cm. Right side stimulating elements 20 and left side stimulating elements 22 are configured such that when coil 1110 is placed on the head, the stimulating elements 20 and 22 lie along a top of a medial portion of the head. The distance D10 between base portion left side 18 and base portion right side 16 is between 4 and 7 cm.

Coil 1110 further includes a return portion 32 including a return portion right side 36 and a return portion left side 38. Return portion right side 36 includes right side return elements 40 which are contacting return elements 50 since they are configured to contact a skull when coil 1110 is in place. Return portion left side 38 includes left side return elements 42 which are also contacting return elements 50. Connecting elements 44 connect right side stimulating elements 20 to right side return elements 40 and connect left side stimulating elements 22 to left side return elements 42. Connecting elements 44 and right and left side return elements 40 and 42 are curved such that right side stimulating elements 20, connecting elements 44 and right side return elements 40 form substantially a circular shape, and left side stimulating elements 22, connecting elements 44 and left side return elements 42 form substantially a circular shape. Each of the circular shapes are configured to lie on a top and side portion of a head.

The distance D5 between base portion right side 16 and return portion right side 36 is approximately 6-7 cm. The distance D6 between base portion left side 18 and return portion left side 38 is approximately 6-7 cm.

Coil 1110 can be configured to be placed on frontal cortex regions such as medial prefrontal cortex or lateral prefrontal cortex, and is used to stimulate medial or lateral cortex regions including unilateral right or left prefrontal cortex regions, and may be useful for treating, for example, attention deficit disorder (ADHD), depression, bipolar disorder and geriatric depression.

Figure 16:
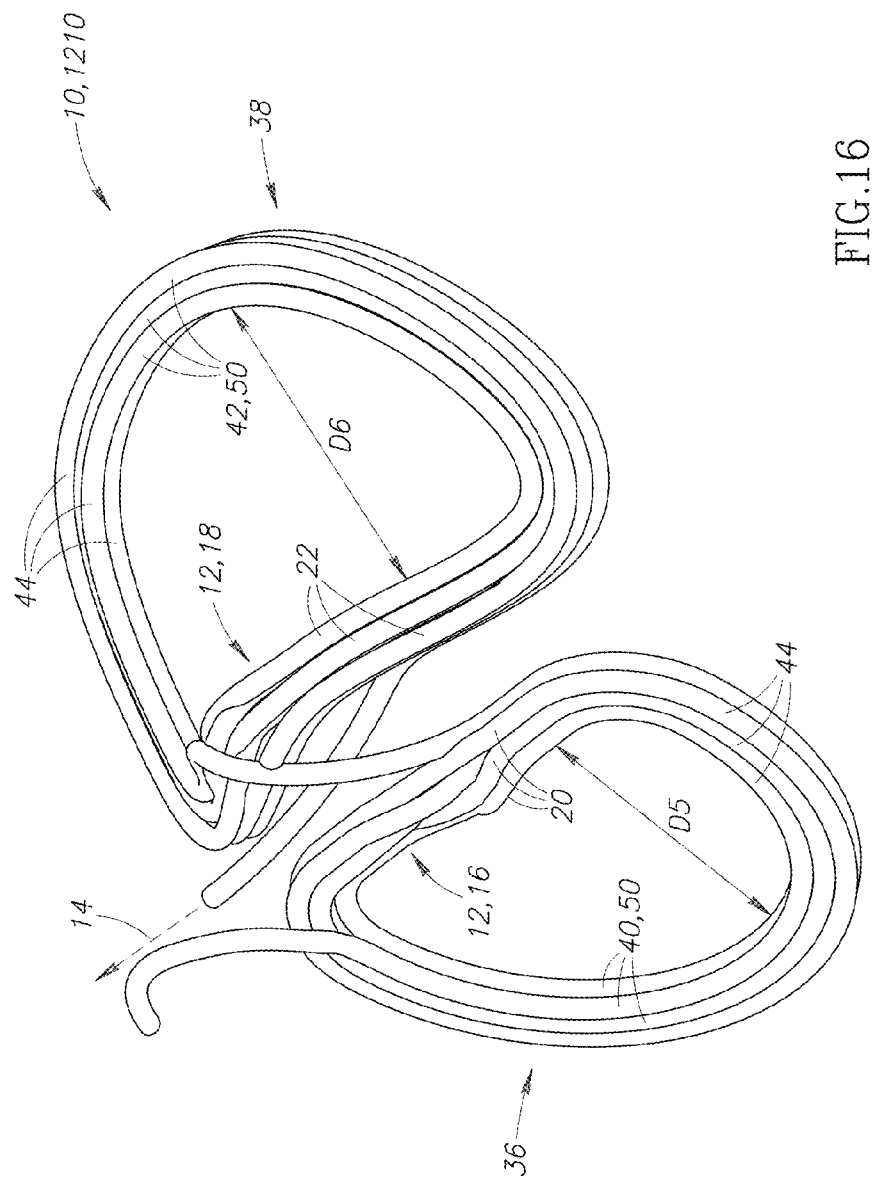
FIG. 16 is a perspective illustration of a coil, which is an example of a central base coil as shown schematically in FIG. 1, in accordance with embodiments of the present invention.

Reference is now made to FIG. 16, which is a perspective illustration of a coil 1210, in accordance with embodiments of the present invention.

Coil 1210 includes a base portion 12 having a base portion right side 16 and a base portion left side 18 on two sides of a central axis 14. Base portion right side 16 includes right side stimulating elements 20. base portion left side 18 includes left side stimulating elements 22, wherein right and left side stimulating elements 20 and 22 are substantially parallel and horizontal with respect to central axis 14. Coil 1210 further includes a return portion 32 including a return portion right side 36 and a return portion left side 38. Return portion right side 36 includes multiple right side return elements 40, and return portion left side 38 includes multiple left side return elements 42. Both right side and left side return elements 40 and 42 are contacting return elements 50. In the embodiment shown herein, base portion 12 is configured to be positioned on a temporal section 106 of head 100, and return portion right side 36 is configured to be positioned above base portion 12, closer to a parietal section 104. Coil 1210 is composed of two circular shapes, with the central groups of both circular shapes—right and left side stimulating elements 20 and 22—forming the base portion. Base portion right side 16 and left side 18 have a distance D5 of approximately 3 cm between them.

Coil 1210 is used to stimulate parietal and temporal lobe brain regions on either right or left hemisphere including the fusiform face area (FFA) and the superior temporal sulcus (STS) and may be useful for treating, for example, autism in children and adults.

Figure 17A:
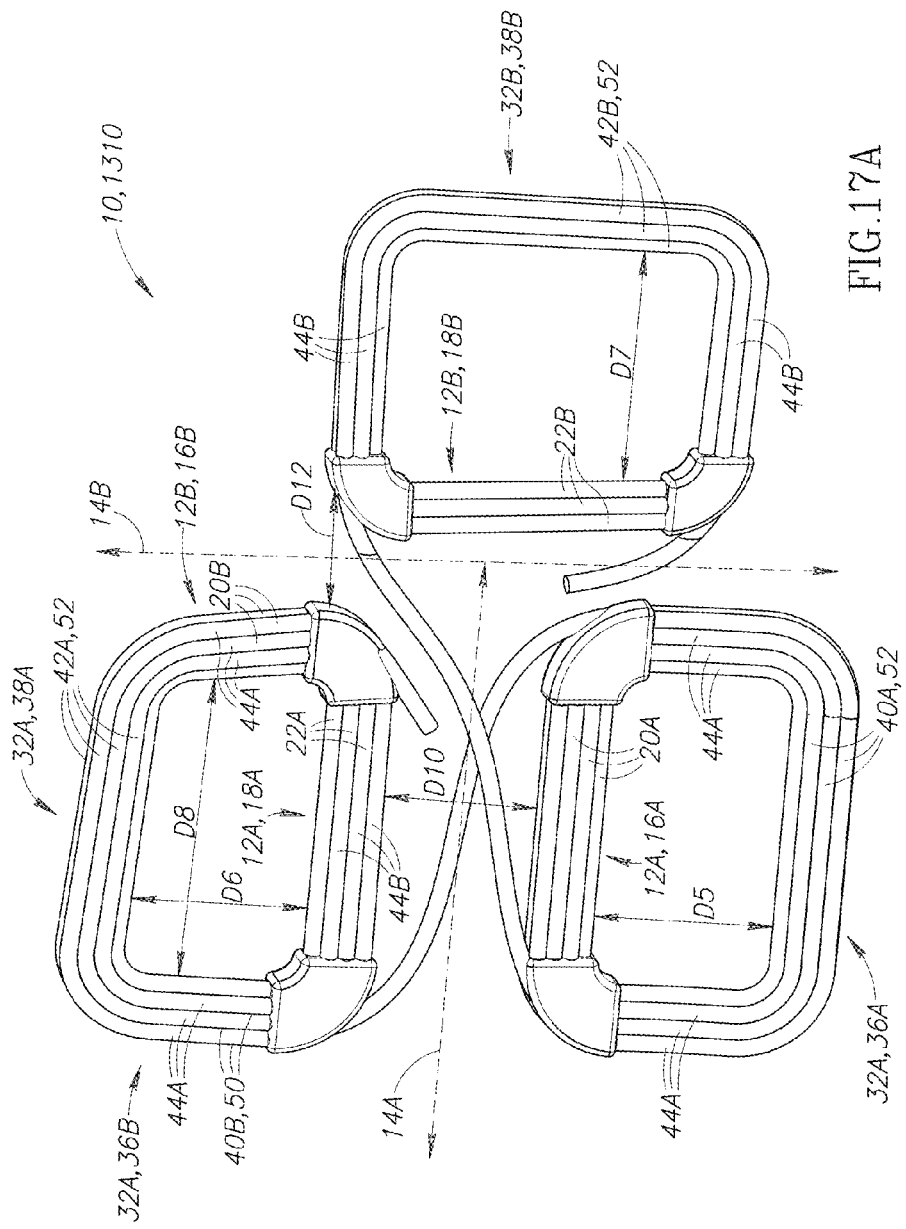
FIGS. 17A-C are perspective illustrations of a coil, which is an example of a central base coil as shown schematically in FIG. 1, in accordance with embodiments of the present invention.

Reference is now made to FIG. 17A, which is a perspective illustration of a coil 1310, in accordance with additional embodiments of the present invention.

Coil 1310 is designed to be placed adjacent to right or left human temple (ie, temporal section 106 of head 100), in order to activate neuronal structures in the right or left insula. Coil 1310 depicted in FIG. 17 is a right coil. A left coil is a mirror image of the right coil depicted in FIG. 17. Coil 1310 includes a first central axis 14A and a second central axis 14B, wherein first and second central axes 14A and 14B are substantially perpendicular to one another. In the embodiment shown herein, first central axis 14 is configured to be positioned along a posterior-anterior direction, and second central axis 14 is configured to be positioned along an inferior-superior axis. A first base portion 12A is positioned substantially parallel to first central axis 14A. First base portion 12A includes a first base portion right side 16A and a first base portion left side 18A, wherein first base portion right side 16A includes multiple first base portion right side stimulating elements 20A, and first base portion left side 18A includes multiple first base portion left side stimulating elements 22A. A second base portion 12B is positioned substantially parallel to second central axis 14B. Second base portion 12B includes a second base portion right side 16B and a second base portion left side 18B, wherein second base portion right side 16B includes multiple second base portion right side stimulating elements 20B, and second base portion left side 18B includes multiple second base portion left side stimulating elements 22B.

Coil 1310 further includes a first return portion 32A corresponding to first base portion 12A and a second return portion 32B corresponding to second base portion 12B. First return portion 32A includes a first return portion right side 36A having first return portion right side return elements 40A, and a first return portion left side 38A having first return portion left side return elements 42A. Connecting elements 44A connect stimulating elements to corresponding return elements. Thus, first base portion right side stimulating elements 20A, connecting elements 44A and first return portion right side return elements 40A form a substantially rectangular shape, and first base portion left side stimulating elements 22A, connecting elements 44A and first return portion left side return elements 42A form a substantially rectangular shape, wherein each rectangular shape is on a side of first central axis 14A. In the embodiment shown herein, the rectangular shape comprised of right side base portion 16A and right side return portion 32A is below first central axis 14A, and the rectangular shape comprised of left side base portion 18A and left side return portion 38A is above first central axis 14A.

Second return portion 32B includes a second return portion right side 36B having second return portion right side return elements 40B, and a second return portion left side 38B having second return portion left side return elements 42B. Connecting elements 44B connect stimulating elements to corresponding return elements. Thus, second base portion right side stimulating elements 20B, connecting elements 44B and second return portion right side return elements 40B form a substantially rectangular shape, and second base portion left side stimulating elements 22B, connecting elements 44B and second return portion left side return elements 42B form a substantially rectangular shape, wherein each rectangular shape is on a side of second central axis 14B. In the embodiment shown herein, the rectangular shape comprised of right side base portion 16B and right side return portion 32B is on one side of second central axis 14B, and is at a vertical distance from the rectangular shape comprised of left side base portion 18B and left side return portion 38B, which is on the other side of second central axis 14B.

In the embodiment shown herein, second base portion right side stimulating elements 20B are also connecting elements 44A connecting first base portion left side stimulating elements 22A to first base portion left side return elements 42A. In addition, first base portion left side stimulating elements 22A and first base portion left side return elements 32A, are also connecting elements 44B connecting second base portion right side stimulating elements 20B to second return portion right side return elements 40B.

Stimulating elements 20A, 20B, 22A and 22B are spaced apart from one another by a distance D1 of approximately 0.3 cm. First base portion right side 16A and first base portion left side 18A are separated from one another by a distance D10 of approximately 4.5 cm. Second base portion right side 16B and second base portion left side are separated from one another by a distance D12 of approximately 4 cm.

A distance D5 between first base portion right side 16A and first return portion right side 36A is approximately 5-6 cm. A distance D6 first base portion left side 18A and second return portion left side 38A is approximately 5-6 cm. A distance D7 between second base portion left side 18B and second return portion left side 38B is approximately 7 cm. A distance D8 between second base portion right side 16B and second return portion right side 36B is approximately 10 cm.

Figure 17B:
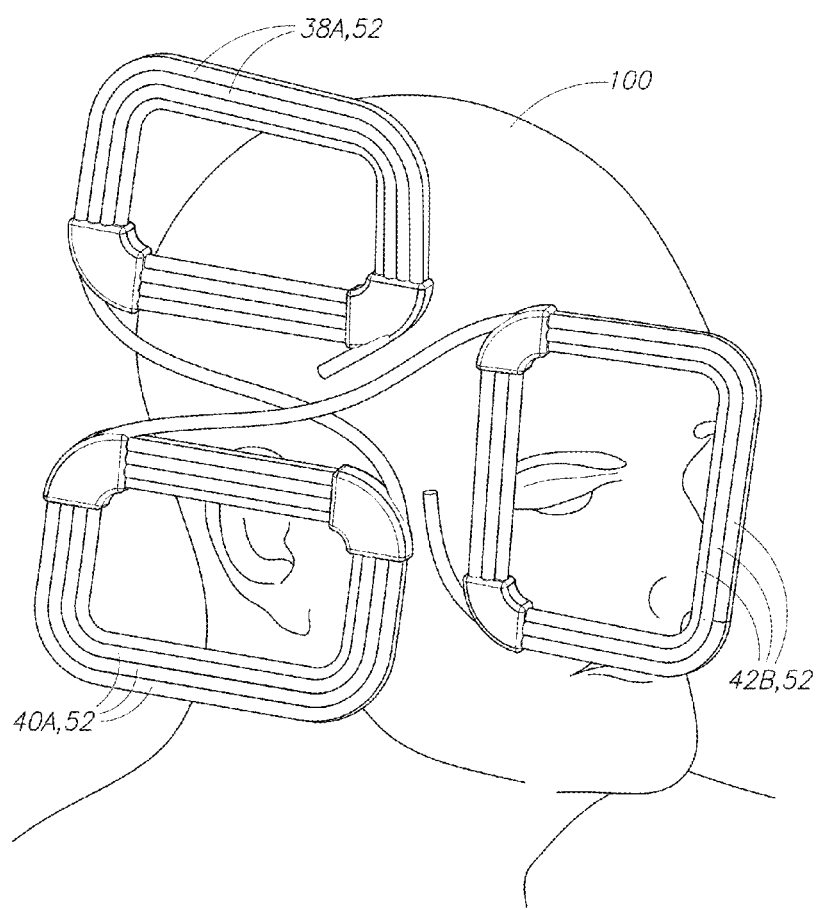
Figure 17C:
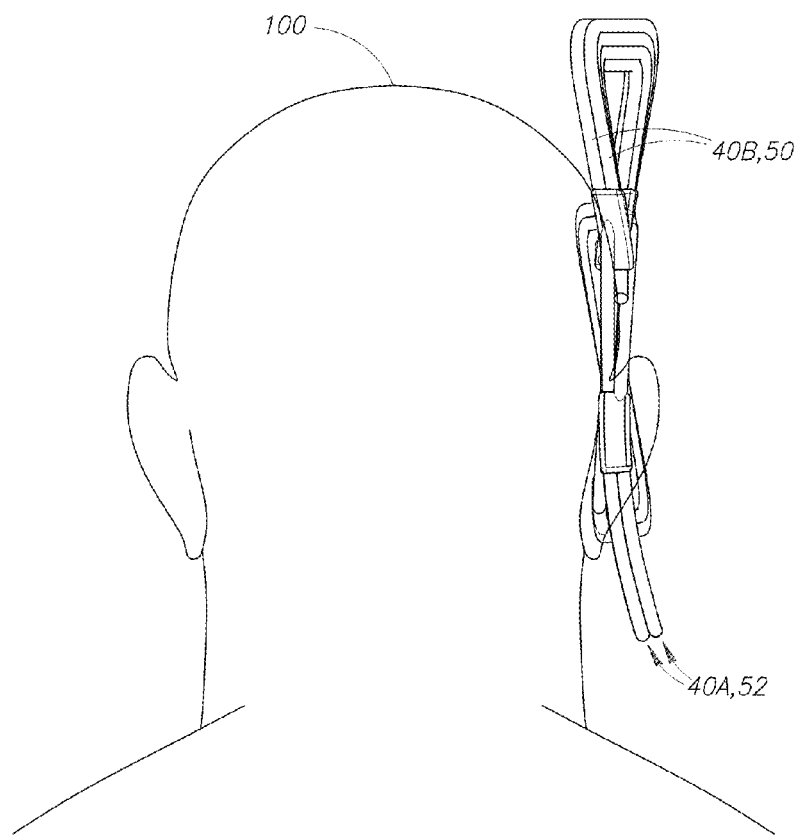

Reference is now made to FIGS. 17B and 17C, which are illustrations showing positioning of coil 1310 on a head 100, from a side view and a rear view, respectively, in accordance with embodiments of the present invention. Second return portion left side 38A is configured to protrude above the medial frontal cortex of the head. First return portion right side return elements 40A are protruding return elements 52, since they are curved away from the head to minimize undesired side effects due to overactivation of the jaw and cheek muscles. Second left side return elements 42B are protruding elements 52 since they are remote from the head and located frontal to the forebrain. Second left side return elements 40B are contacting return elements 50 and are configured to contact the head at parietal and temporal cortex regions.

Coil 1310 can be used to stimulate unilaterally regions in the right or left insular cortex and entorhinal cortex, and may be useful for treating, for example, obesity, anorexia nervosa, bulimia, other eating disorders, various types of addiction including smoking addiction, drug addiction, alcoholism, and also for treating schizophrenic subjects suffering from auditory hallucinations.

EXAMPLES

In order for the designs of the central base coils described above to be effective, the designs must be efficient with respect to energy consumption, coil heating rate, compact size and ease of operation, and must guarantee that the motor threshold and stimulation intensity for most of the relevant population is within an acceptable range with respect to available stimulators power outputs. In order to test these parameters and the efficacy of each coil for the particular indication, the following experiments were carried out.

Figure 18:
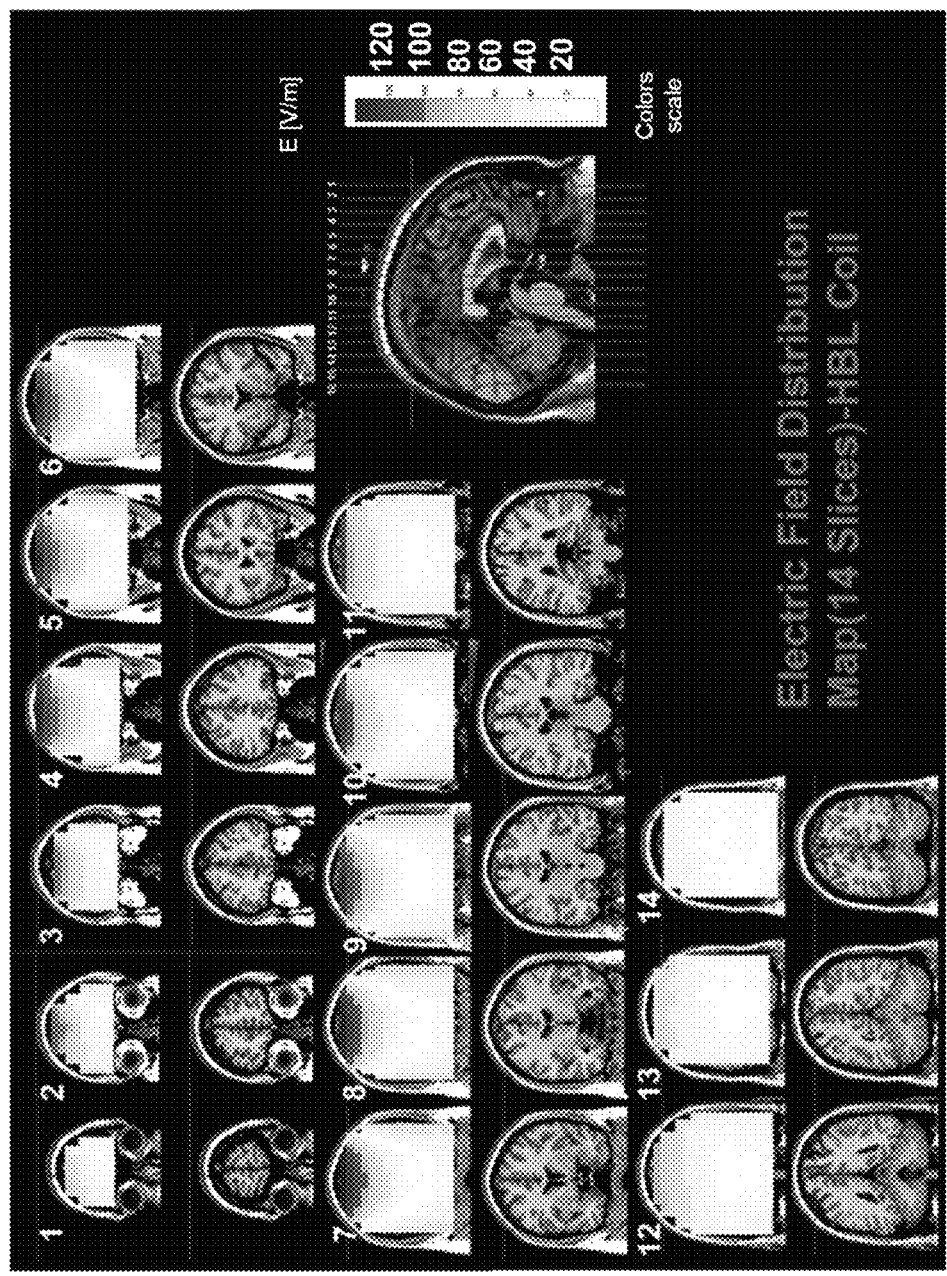
FIG. 18 is an illustration of electric field distribution maps of the coil of FIG. 5 as measured in a human head phantom model.

Reference is now made to FIG. 18, which is an illustration of electric field distribution maps of coil 110 of FIG. 5. The field distribution produced by coil 110 was measured in a human head phantom model. The probe was moved in three directions inside the phantom model using a displacement system with 1 mm resolution, and the field distribution of coil 110 was measured in the whole head model volume in 1 cm resolution. Axial and coronal field maps were produced. The field maps were superimposed on anatomical T1-weighted MRI coronal slices, to show the induced field in each anatomical brain region. The field maps are shown for stimulator output set at 100% of leg threshold. The dark pixels indicate field magnitude above the threshold for neuronal activation. The threshold was set to 100 V/m, which is within the accepted range of thresholds required for motor activation. The intensity of stimulator power output used for drawing the maps representing the distribution of the electric field for each coil was set to the level required to obtain 100% of the neural motor threshold, at a depth of 3 cm, according to the approximate depth of leg motor cortex sites. It can be seen that when placing the base portion of the coil over the prefrontal cortex, supra-threshold field is induced bilaterally in medial prefrontal regions including the anterior cingulate.

Figure 19:
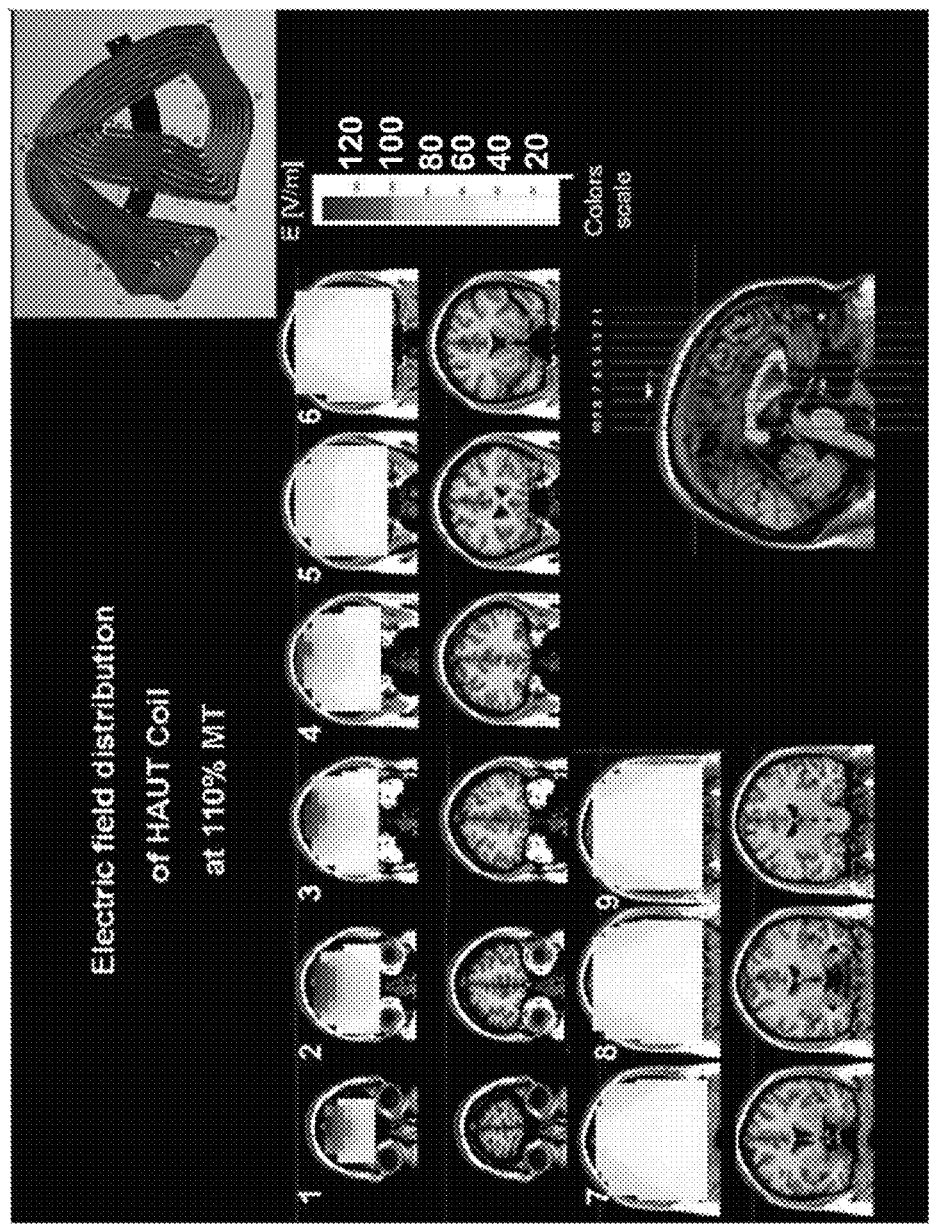
FIG. 19 is an illustration of electric field distribution maps of the coil of FIG. 6 as measured in a human head phantom model.

Reference is now made to FIG. 19, which is an illustration of electric field distribution maps of coil 210 of FIG. 6. The field distribution produced by coil 210 was measured using the method described above with reference to FIG. 18. The field maps are shown for stimulator output set at 110% of hand motor threshold. It can be seen that when placing the base portion of the coil over the prefrontal cortex, supra-threshold field is induced bilaterally in medial prefrontal and orbitofrontal regions including the paracingulate cortex.

Figure 20:
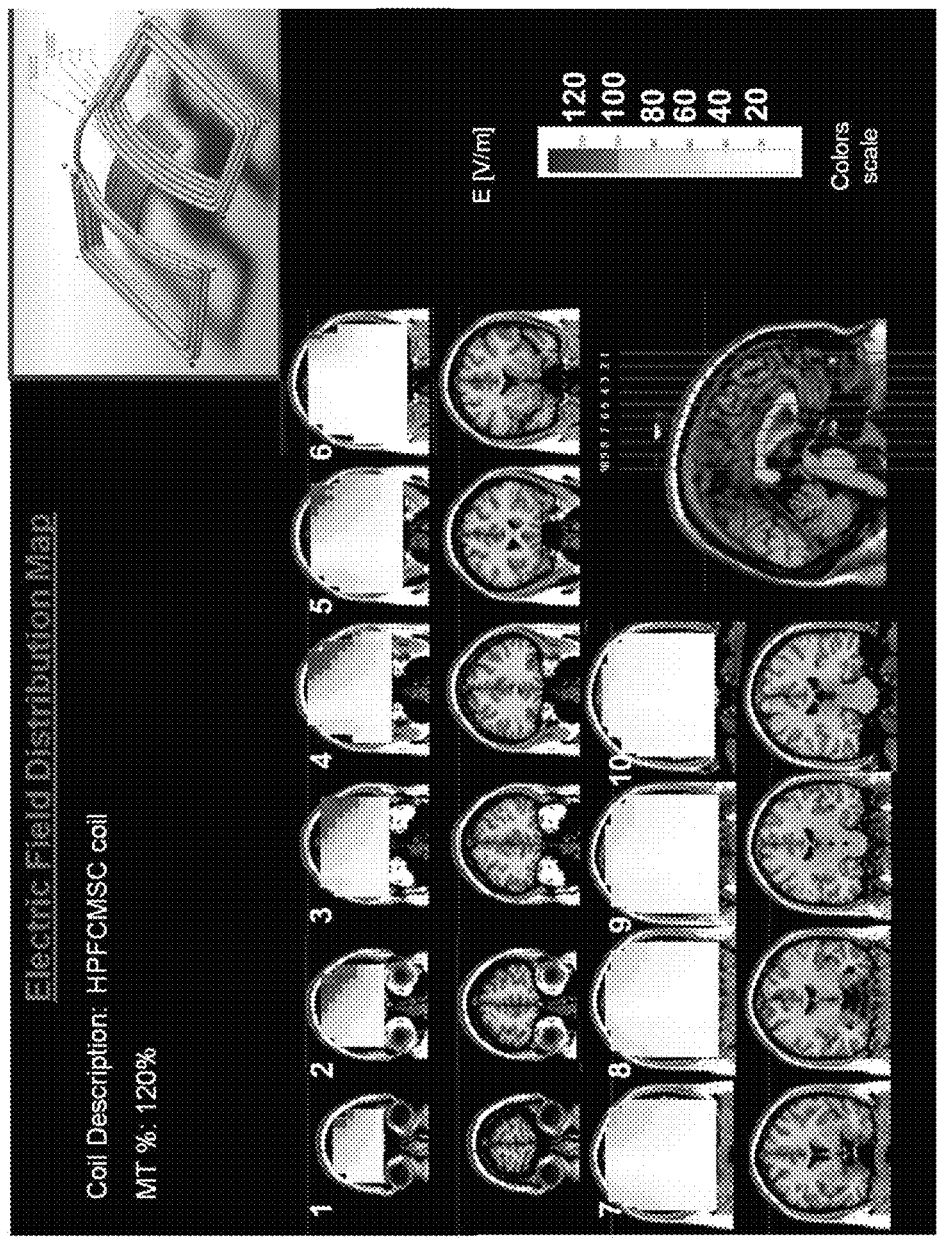
FIG. 20 is an illustration of electric field distribution maps of the coil of FIG. 7 as measured in a human head phantom model.

Reference is now made to FIG. 20, which is an illustration of electric field distribution maps of coil 310 of FIG. 7. The field distribution produced by coil 310 was measured using the method described above with reference to FIG. 18. The field maps are shown for stimulator output set at 120% of hand motor threshold. It can be seen that when placing the base portion of the coil over the prefrontal cortex, supra-threshold field is induced in lateral and medial prefrontal regions of either right or left hemisphere.

Figure 21:
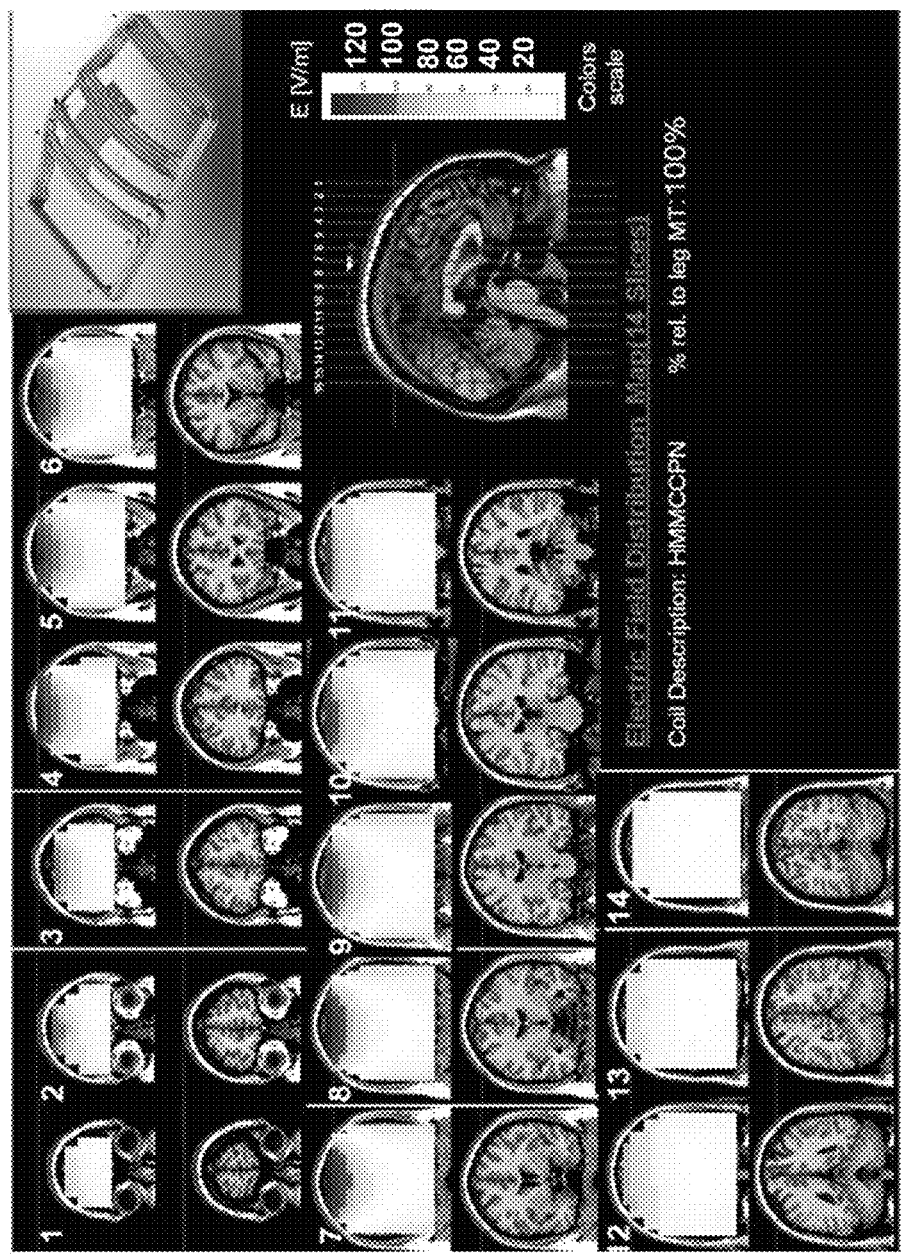
FIG. 21 is an illustration of electric field distribution maps of the coil of FIG. 8 as measured in a human head phantom model.

Reference is now made to FIG. 21, which is an illustration of electric field distribution maps of coil 410 of FIG. 8. The field distribution produced by coil 410 was measured using the method described above with reference to FIG. 18. The field maps are shown for stimulator output set at 100% of leg motor threshold. It can be seen that when placing the base portion of the coil over the motor cortex, supra-threshold field is induced bilaterally in lateral and medial motor cortex regions.

Figure 22:
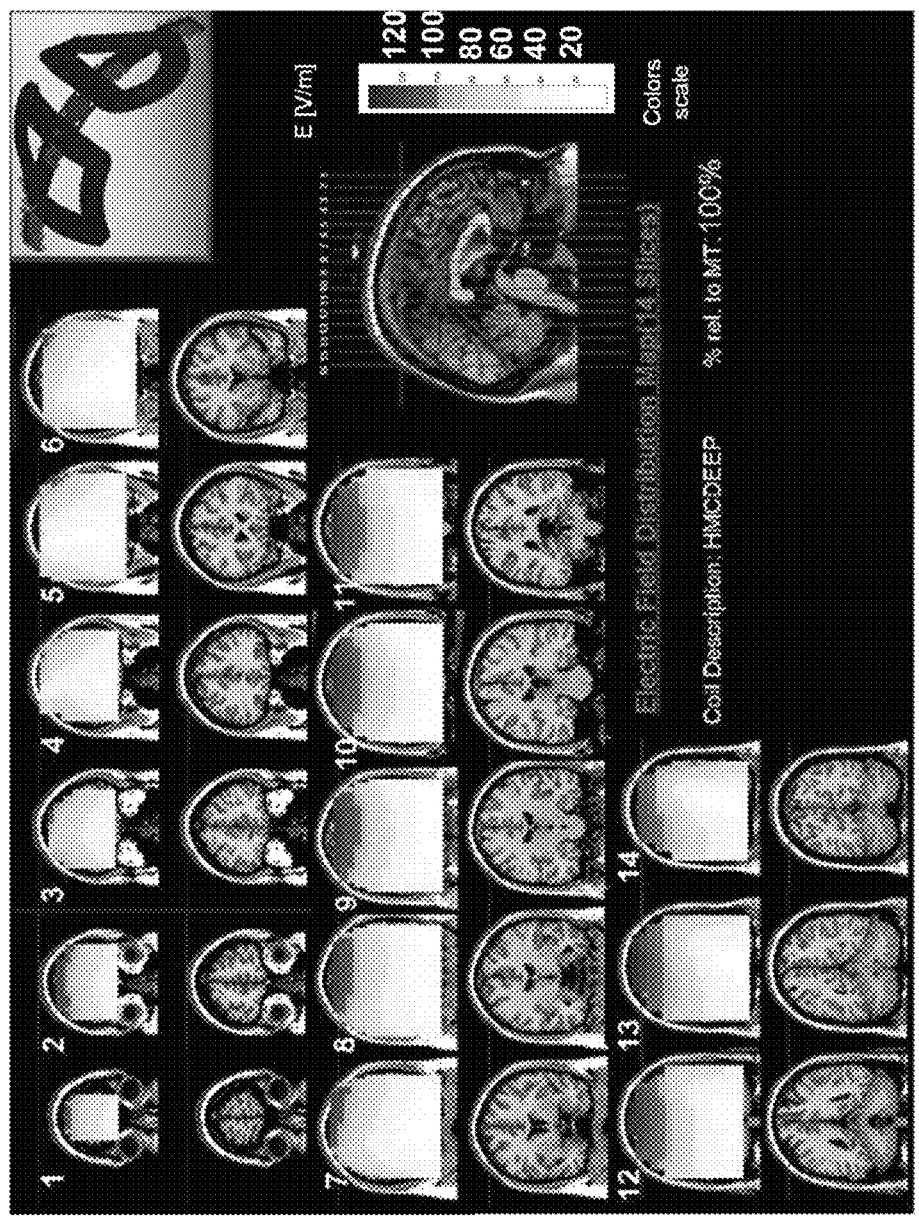
FIG. 22 is an illustration of electric field distribution maps of the coil of FIG. 9 as measured in a human head phantom model.

Reference is now made to FIG. 22, which is an illustration of electric field distribution maps of coil 510 of FIG. 9. The field distribution produced by coil 510 was measured using the method described above with reference to FIG. 18. The field maps are shown for stimulator output set at 100% of leg motor threshold. It can be seen that when placing the base portion of the coil over the motor cortex, supra-threshold field is induced bilaterally in lateral and medial motor cortex regions.

Figure 23:
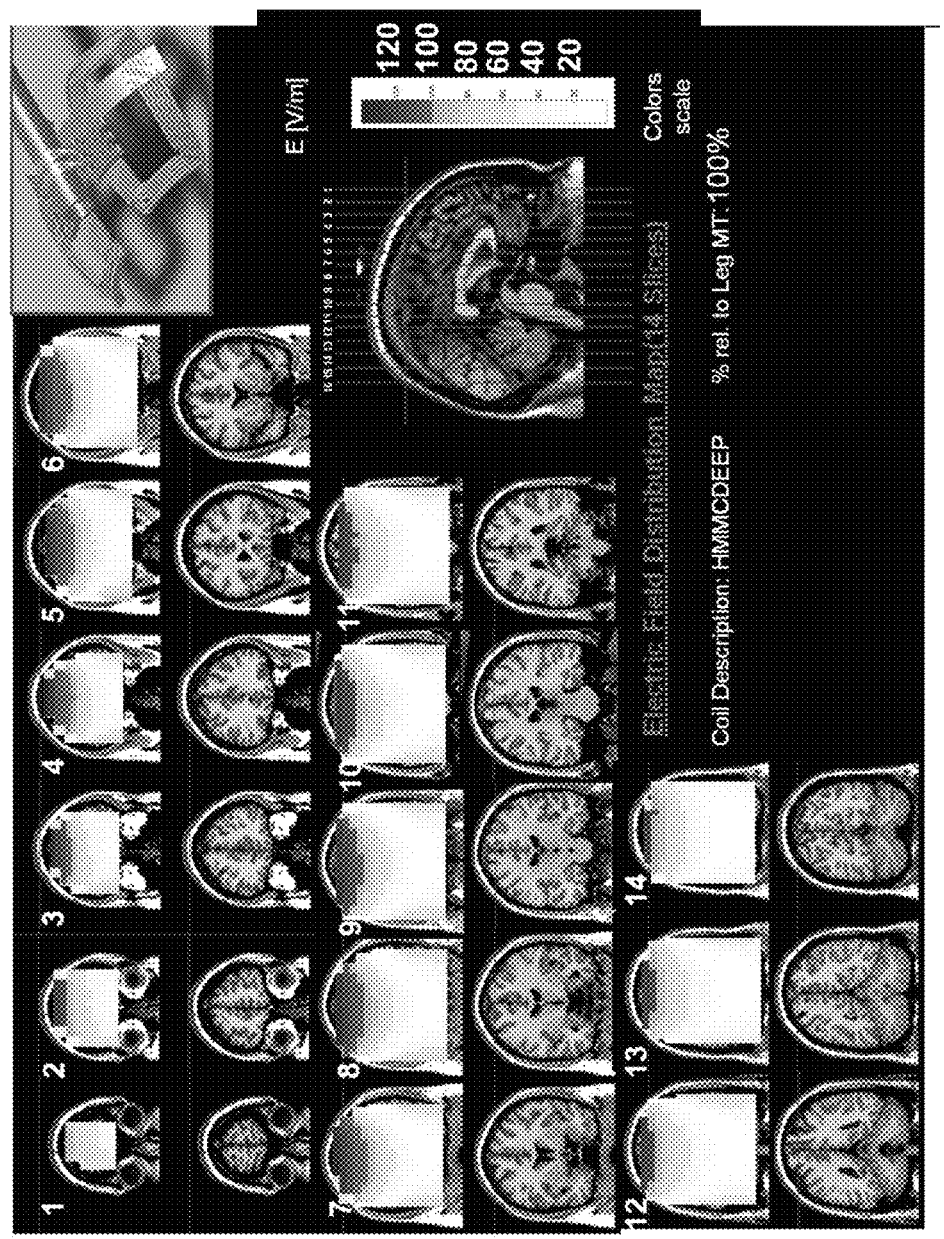
FIG. 23 is an illustration of electric field distribution maps of the coil of FIG. 10 as measured in a human head phantom model.

Reference is now made to FIG. 23, which is an illustration of electric field distribution maps of coil 610 of FIG. 10. The field distribution produced by coil 610 was measured using the method described above with reference to FIG. 18. The field maps are shown for stimulator output set at 100% of leg motor threshold. It can be seen that when placing the base portion of the coil over the motor cortex, supra-threshold field is induced bilaterally in lateral and medial motor cortex regions.

Figure 24:
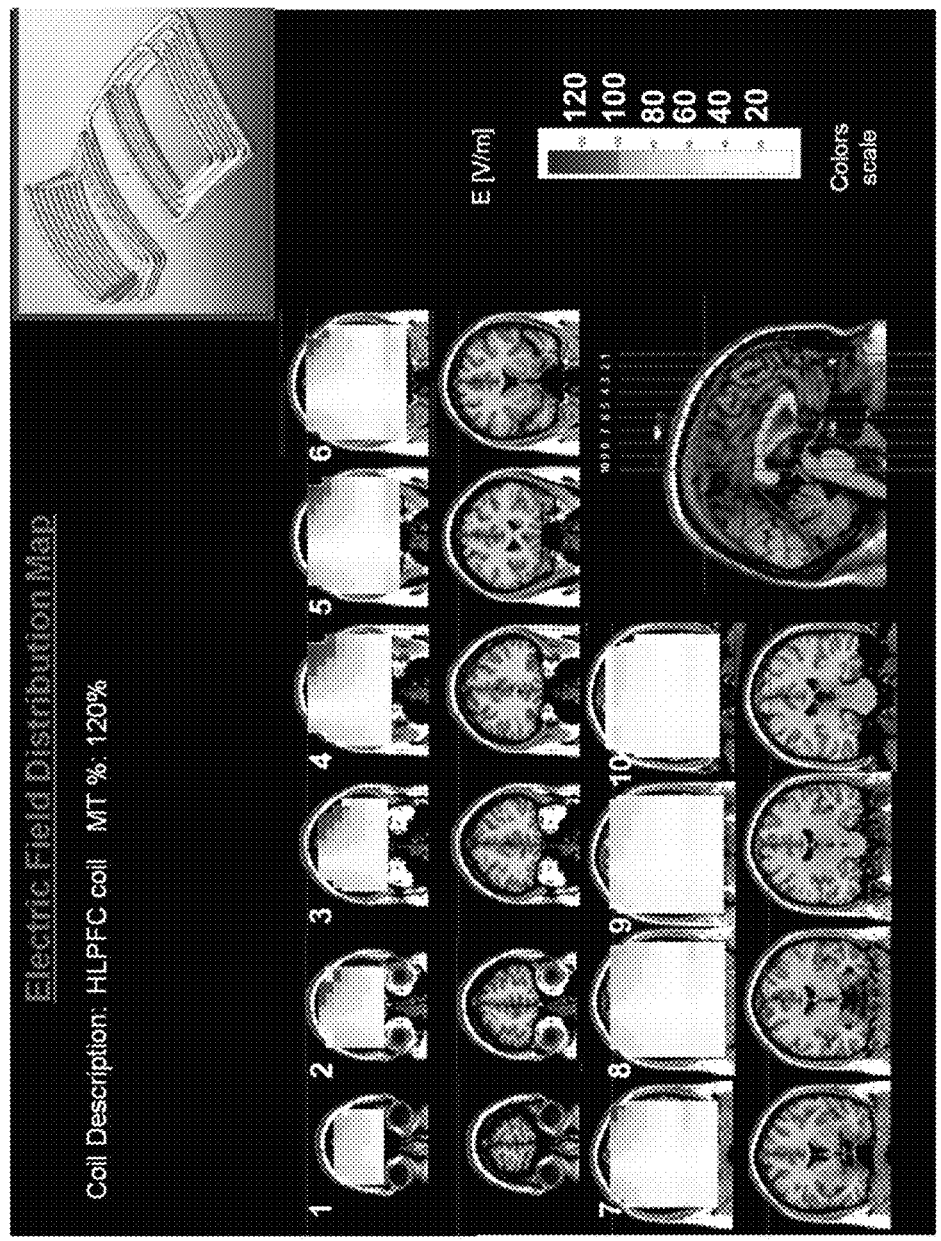
FIG. 24 is an illustration of electric field distribution maps of the coil of FIG. 11 as measured in a human head phantom model.

Reference is now made to FIG. 24, which is an illustration of electric field distribution maps of coil 710 of FIG. 11. The field distribution produced by coil 710 was measured using the method described above with reference to FIG. 18. The field maps are shown for stimulator output set at 120% of hand motor threshold. It can be seen that when placing the base portion of the coil over the prefrontal cortex, supra-threshold field is induced in lateral and medial prefrontal regions of either right or left hemisphere.

Figure 25:
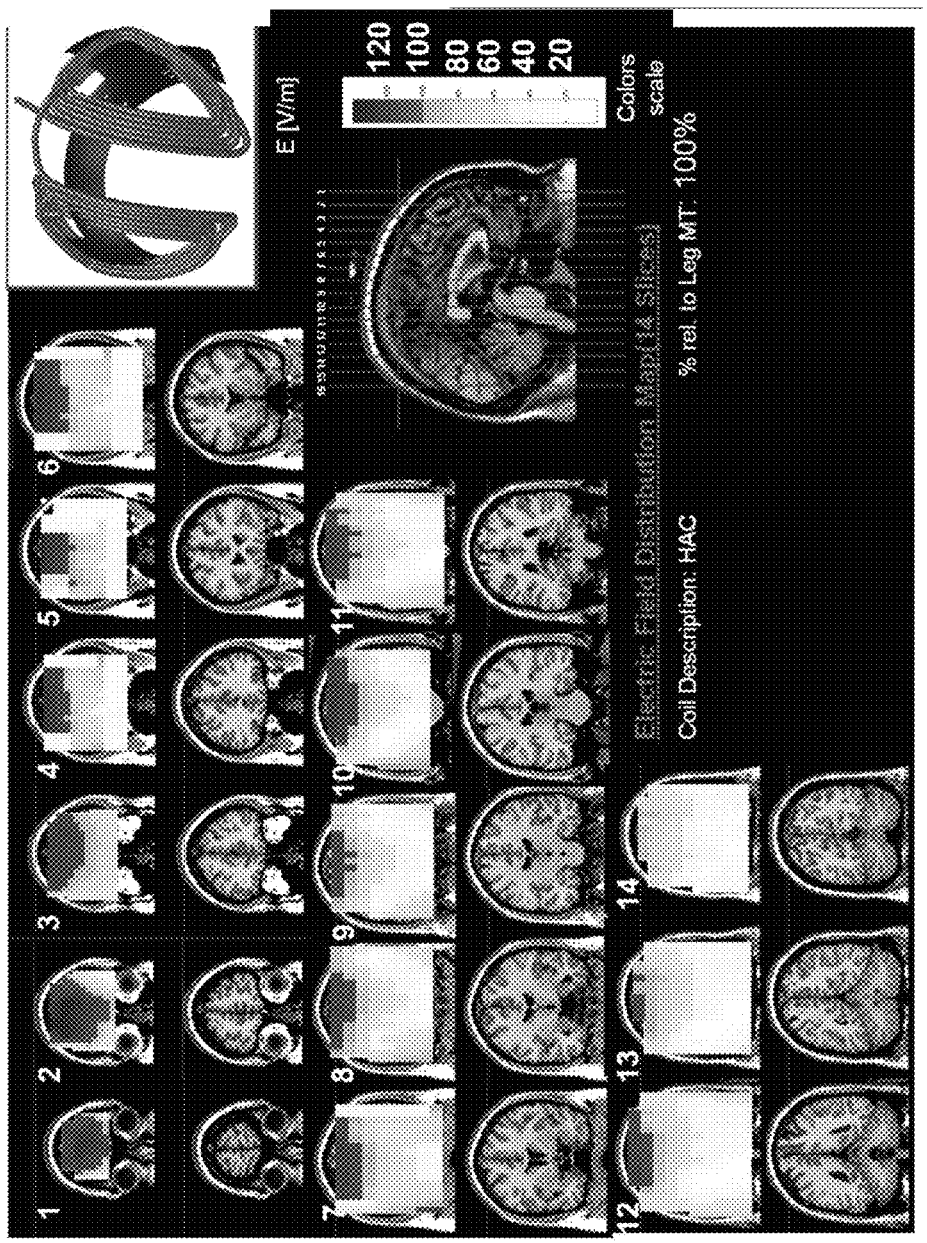
FIG. 25 is an illustration of electric field distribution maps of the coil of FIG. 12 as measured in a human head phantom model.

Reference is now made to FIG. 25, which is an illustration of electric field distribution maps of coil 810 of FIG. 12. The field distribution produced by coil 810 was measured using the method described above with reference to FIG. 18. The field maps are shown for stimulator output set at 100% of leg motor threshold. It can be seen that when placing the base portion of the coil over the prefrontal cortex, supra-threshold field is induced bilaterally in medial prefrontal regions including the anterior cingulate cortex. Coil 810 is being used in a clinical study testing the safety and efficacy of this device in treating subjects suffering from cocaine addiction, Tourette's syndrome, chronic pain and OCD. Interim results from the OCD study of 9 subjects suffering from OCD showed that 40% subjects showed response (defined as at least 35% improvement in YBOCS questionnaire), while no improvement was found in the placebo control group.

Figure 26:
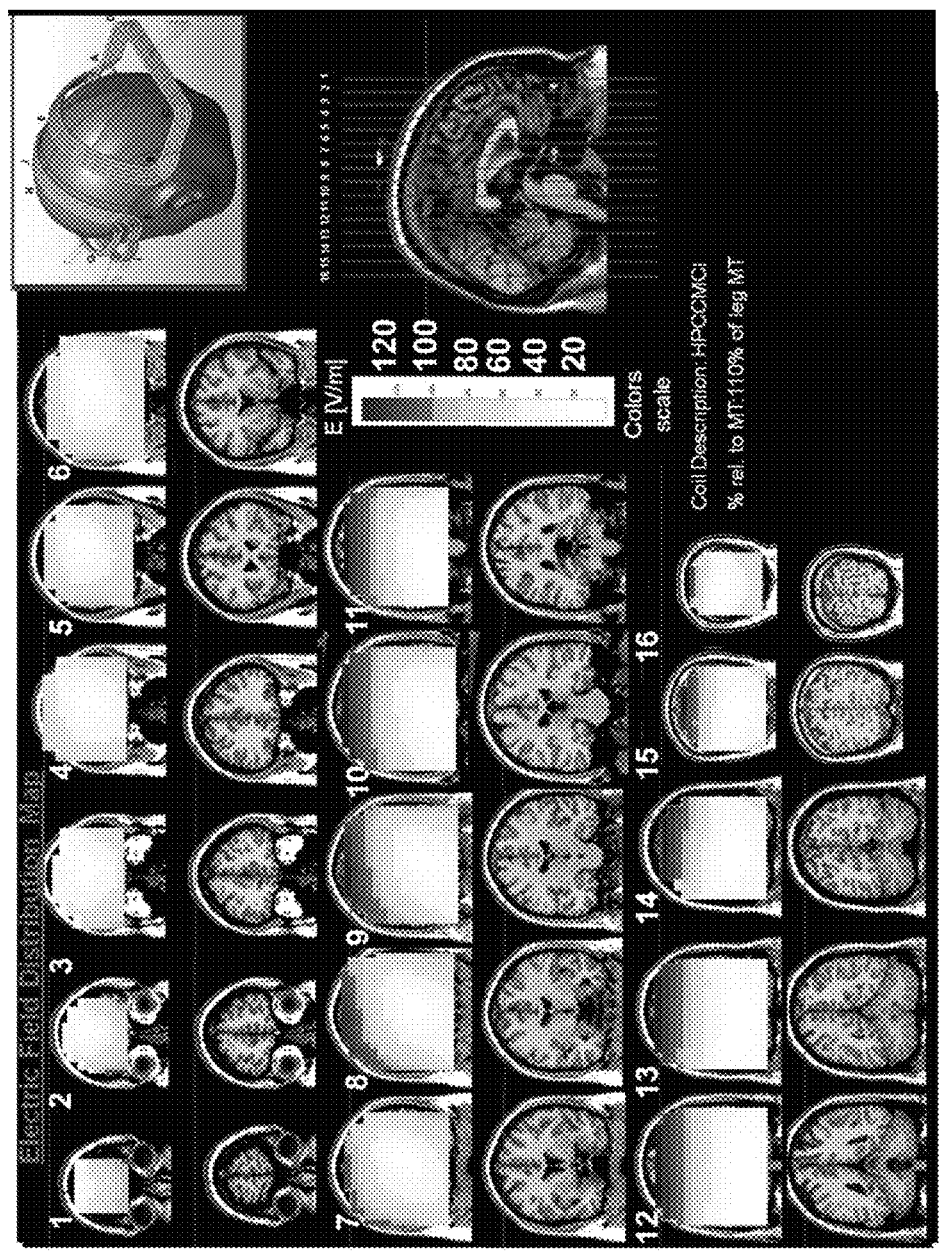
FIG. 26 is an illustration of electric field distribution maps of the coil of FIGS. 13A and 13B as measured in a human head phantom model.

Reference is now made to FIG. 26, which is an illustration of electric field distribution maps of coil 910 of FIGS. 13A and 13B. The field distribution produced by coil 910 was measured using the method described above with reference to FIG. 18. The field maps are shown for stimulator output set at 110% of leg motor threshold. It can be seen that when placing the base portion of the coil over the parietal cortex, supra-threshold field is induced bilaterally in medial parietal regions including the posterior cingulate cortex.

Figure 27:
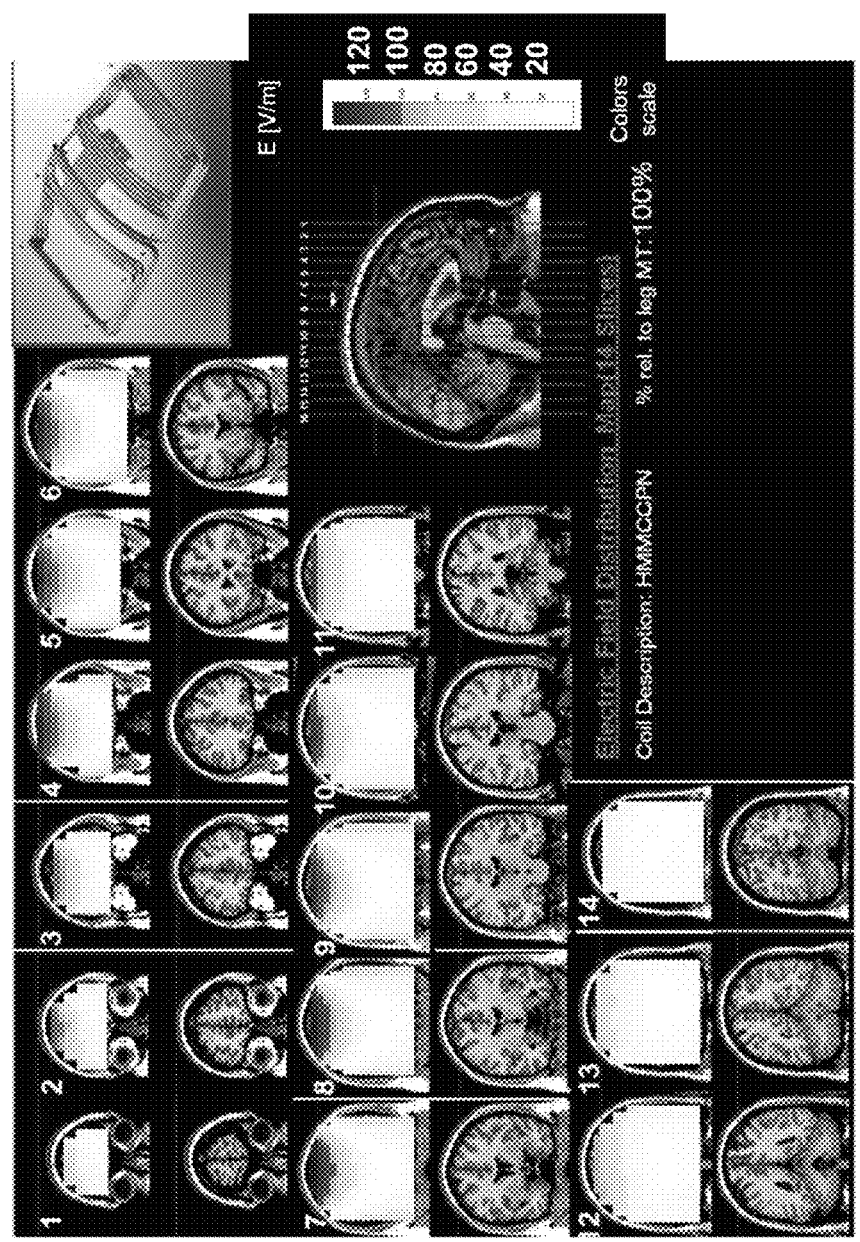
FIG. 27 is an illustration of electric field distribution maps of the coil of FIG. 14 as measured in a human head phantom model.

Reference is now made to FIG. 27, which is an illustration of electric field distribution maps of coil 1010 of FIG. 14. The field distribution produced by coil 1010 was measured using the method described above with reference to FIG. 18. The field maps are shown for stimulator output set at 100% of leg motor threshold. It can be seen that when placing the base portion of the coil over the motor cortex, supra-threshold field is induced bilaterally in medial and lateral motor cortex regions.

Figure 28:
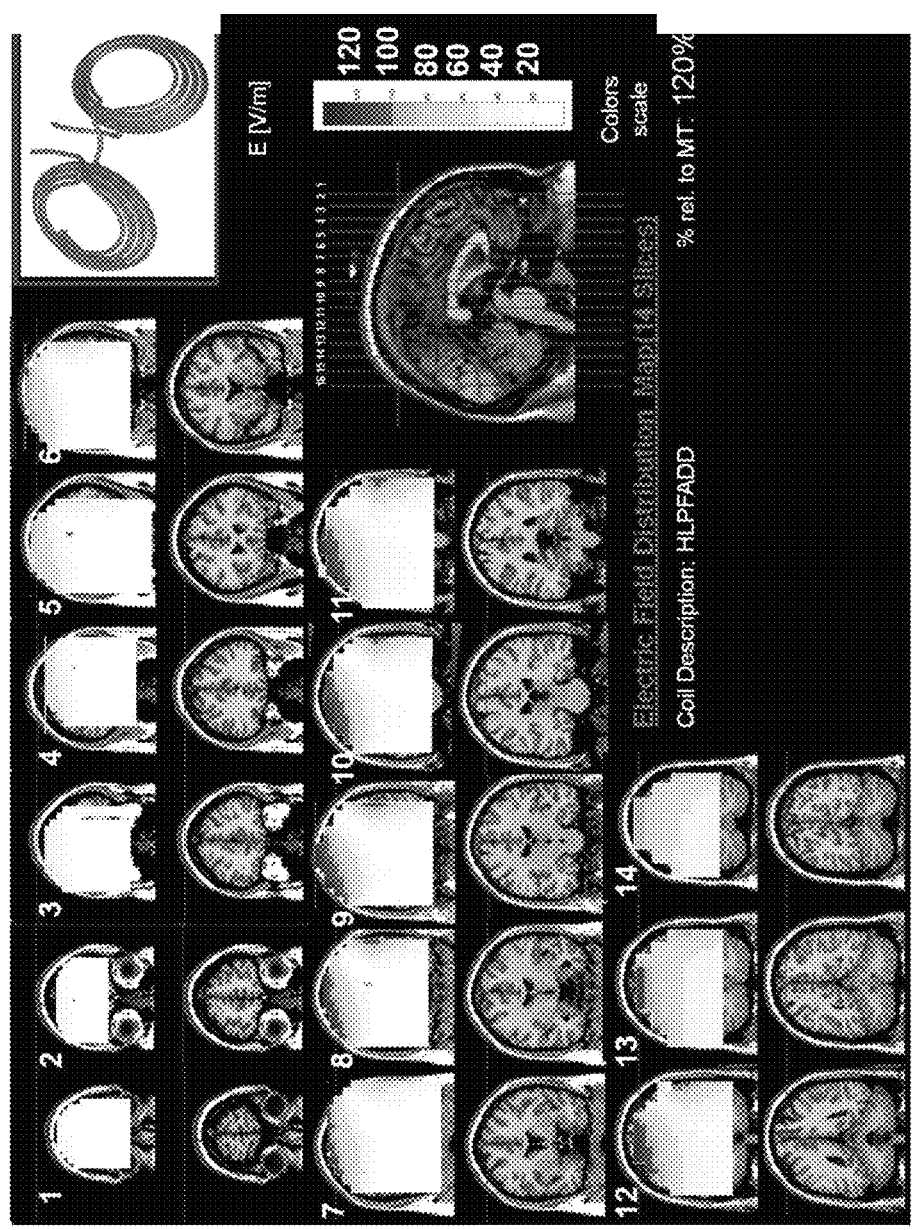
FIG. 28 is an illustration of electric field distribution maps of the coil of 15 as measured in a human head phantom model.

Reference is now made to FIG. 28, which is an illustration of electric field distribution maps of coil 1110 of FIG. 15. The field distribution produced by coil 1110 was measured using the method described above with reference to FIG. 18. The field maps are shown for stimulator output set at 120% of hand motor threshold. It can be seen that when placing the base portion of the coil over the prefrontal cortex, supra-threshold field is induced in lateral and medial prefrontal regions of either right or left hemisphere.

Figure 29:
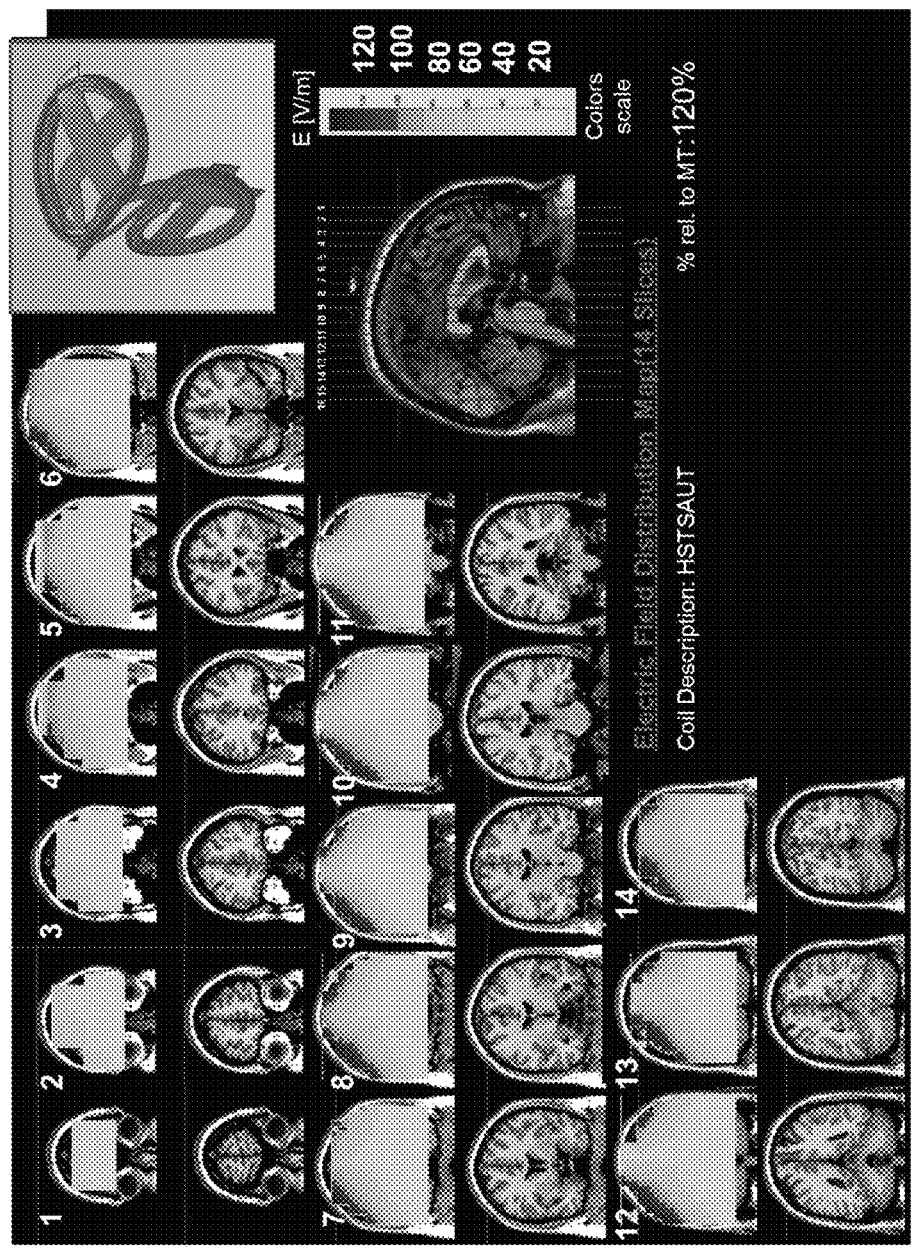
FIG. 29 is an illustration of electric field distribution maps of the coil of FIG. 16 as measured in a human head phantom model.

Reference is now made to FIG. 29, which is an illustration of electric field distribution maps of coil 1210 of FIG. 16. The field distribution produced by coil 1210 was measured using the same method as for FIG. 18. The field maps are shown for stimulator output set at 120% of motor threshold. It can be seen that when placing the coil over the right parietal cortex, supra-threshold field is induced mainly at right parietal and temporal regions including deeper regions.

Figure 30:
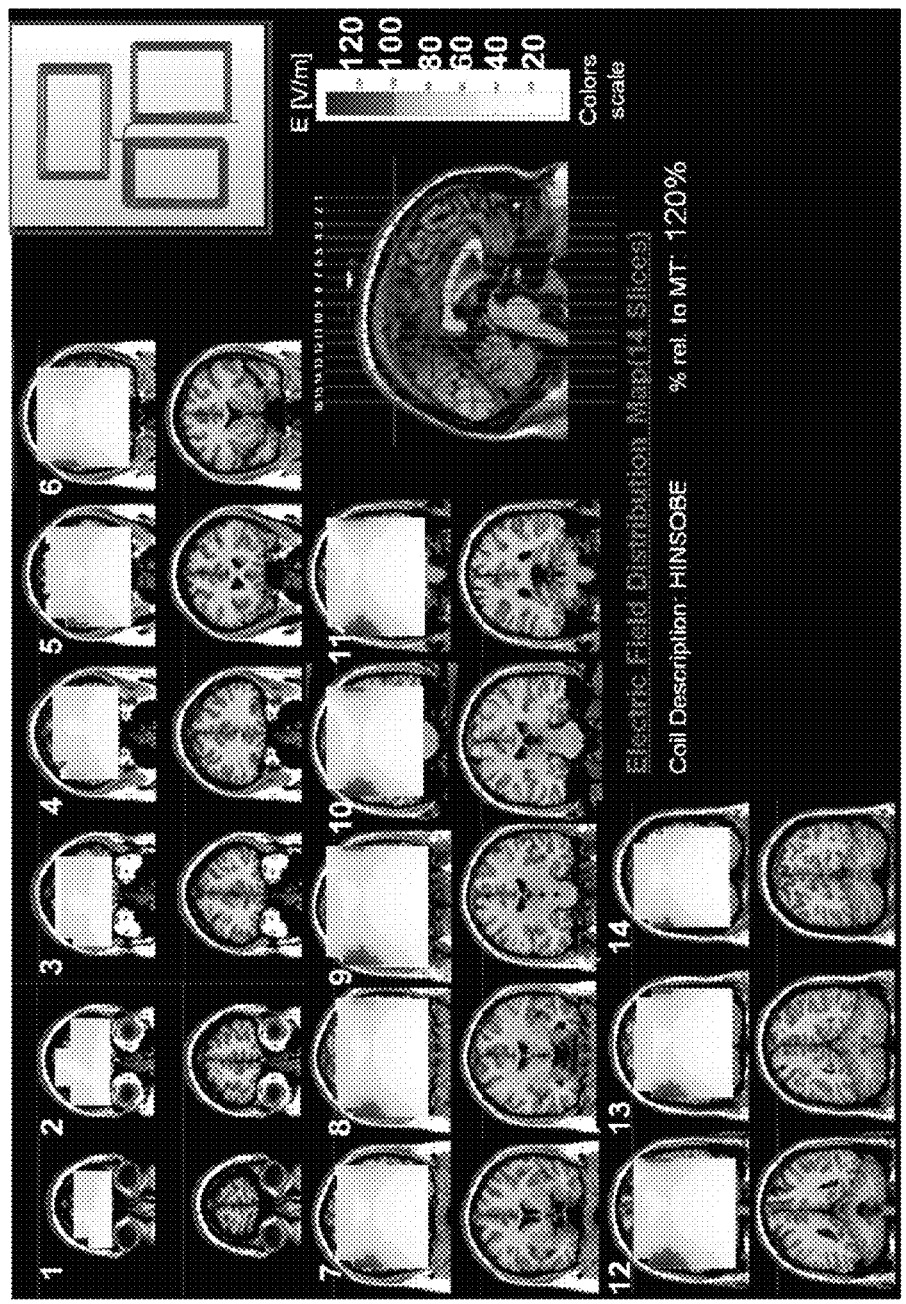
FIG. 30 is an illustration of electric field distribution maps of the coil of FIG. 17 as measured in a human head phantom model.

Reference is now made to FIG. 30, which is an illustration of electric field distribution maps of coil 1310 of FIG. 17A. The field distribution produced by coil 1310 was measured using the method described above with reference to FIG. 18. The field maps are shown for stimulator output set at 120% of hand motor threshold. It can be seen that when placing the base portion of the coil over the temporal cortex, supra-threshold field is induced in lateral prefrontal and temporal regions of the relevant hemisphere including insular and entorhinal cortex regions.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

While certain features of the present invention have been illustrated and described herein, many modifications, substitutions, changes, and equivalents may occur to those of ordinary skill in the art. It is, therefore, to be understood that the appended claims are intended to cover all such modifications and changes as fall within the true spirit of the present invention.

What is claimed is:

1. A coil for magnetic stimulation, the coil comprising:
    a base portion including
        a central axis defining a base portion right side and a base portion left side, wherein said base portion right side is positioned on a right side of said central axis and said base portion left side is positioned on a left side of said central axis,
        multiple right side stimulating elements, said right side stimulating elements positioned in said base portion right side, wherein said multiple right side stimulating elements are substantially parallel to one another, said multiple right side stimulating elements configured to carry electrical current in substantially a first direction, and
        multiple left side stimulating elements, said left side stimulating elements positioned in said base portion left side, wherein said multiple left side stimulating elements are substantially parallel to one another, said multiple left side stimulating elements configured to carry electrical current in substantially said first direction; and
    a return portion including
        multiple right side return elements positioned on the right side of said central axis, wherein each of said right side return elements corresponds to one of said multiple right side stimulating elements and wherein each of said right side return elements is positioned further away from said central axis than its corresponding right side stimulating element, wherein said multiple right side return elements are substantially parallel to one another, and wherein each of said multiple right side return elements is configured to carry electrical current in substantially a second direction, wherein said second direction is an opposite direction to said first direction, and
        multiple left side return elements positioned on the left side of said central axis, wherein each of said left side return elements corresponds to one of said multiple left side stimulating elements and wherein each of said left side return elements is positioned further away from said central axis than its corresponding left side stimulating element, wherein said multiple left side return elements are substantially parallel to one another, and wherein each of said multiple left side return elements is configured to carry electrical current in substantially said second direction,
    wherein said return portion is spaced a distance away from said base portion.

2. The coil of claim 1, wherein said multiple right side stimulating elements includes a number of elements which is equal to a number of said multiple left side stimulating elements.

3. The coil of claim 1, wherein said multiple right side stimulating elements are spaced apart from one another and wherein said multiple left side stimulating elements are spaced apart from one another.

4. The coil of claim 3, wherein said multiple right side stimulating elements are spaced variably from one another.

5. The coil of claim 4, wherein said multiple right side stimulating elements include multiple right side groupings of stimulating elements, and wherein said multiple right side groupings are spaced apart from one another.

6. The coil of claim 5, wherein said multiple right side groupings are spaced variably from one another.

7. The coil of claim 5, wherein said multiple right side groupings are spaced uniformly from one another.

8. The coil of claim 3, wherein said multiple left side stimulating elements are spaced variably from one another.

9. The coil of claim 8, wherein said multiple left side stimulating elements include multiple left side groupings of stimulating elements, and wherein said multiple left side groupings are spaced apart from one another.

10. The coil of claim 9, wherein said multiple left side groupings are spaced variably from one another.

11. The coil of claim 9, wherein said multiple left side groupings are spaced uniformly from one another.

12. The coil of claim 1, wherein said multiple right side return elements are spaced apart from one another and wherein said multiple left side return elements are spaced apart from one another.

13. The coil of claim 1, wherein at least one of: some of said multiple right side return elements are configured to contact a body part and some of said multiple right side return elements are configured to be placed at a distance from a body part and all of said left side return elements are configured to contact a body part; some of said multiple right side return elements are configured to contact a body part and some of said multiple right side return elements are configured to be placed at a distance from a body part and all of said left side return elements are configured to be placed at a distance from a body part; some of said multiple left side return elements are configured to contact a body part and some of said multiple left side return elements are configured to be placed at a distance from a body part and all of said right side return elements are configured to contact a body part; and some of said multiple left side return elements are configured to contact a body part and some of said multiple left side return elements are configured to be placed at a distance from a body part and all of said right side return elements are configured to be placed at a distance from a body part.

14. The coil of claim 1, wherein at least one of: some of said multiple right side return elements and some of said multiple left side return elements are configured to contact a body part; some of said multiple right side return elements and some of said multiple left side return elements are configured to be placed at a distance from a body part; all of said multiple right side return elements and said left side return elements are configured to contact a body part; and all of said multiple right side return elements and said left side return elements are configured to be placed at a distance from a body part.

15. The coil of claim 1, wherein said base portion includes a first base portion and a second base portion, wherein said first base portion includes a first central axis, said multiple right side stimulating elements on a right side of said first central axis, and said multiple left side stimulating elements on a left side of said first central axis, and wherein said second base portion includes a second central axis, additional multiple right side stimulating elements on a right side of said second central axis, and additional multiple left side stimulating elements on a left side of said second central axis.

16. The coil of claim 15, wherein said first central axis runs along a different direction than said second central axis.

17. The coil of claim 16, wherein said first central axis is substantially perpendicular to said second central axis.

18. The coil of claim 1, further comprising: a right side connecting portion including multiple right side connecting elements positioned on the right side of the central axis, wherein each of said right side connecting elements is configured to carry electrical current from one of said multiple right side stimulating elements to the corresponding right side return element in a first rotational direction; and a left side connecting portion including multiple left side connecting elements positioned on the left side of the central axis, wherein each of said left side connecting elements is configured to carry electrical current from one of said multiple left side stimulating elements to the corresponding left side return element in a second rotational direction which is opposite the first rotational direction.

19. A method for treating a neurophysiological condition, the method comprising:

identifying a subject suffering from a neurophysiological condition;

placing a coil on said subject's head, the coil including a base portion having a central axis defining a base portion right side on a right side of the central axis and a base portion left side on a left side of the central axis, multiple right side stimulating elements in said base portion right side, said multiple right side stimulating elements substantially parallel to one another and configured to carry electrical current in substantially a first direction, multiple left side stimulating elements in said base portion left side, said multiple left side stimulating elements substantially parallel to one another and configured to carry electrical current in substantially the first direction, and a return portion having multiple right side return elements positioned on the right side of central axis, wherein each of the right side return elements corresponds to one of the multiple right side stimulating elements, and wherein each of the right side return elements is positioned further away from the central axis than its corresponding right side stimulating element, wherein each of the multiple right side return elements is configured to carry electrical current in substantially a second direction, wherein the second direction is an opposite direction to the first direction, the return portion further including multiple left side return elements positioned on the left side of the central axis, wherein each of the left side return elements corresponds to one of the multiple left side stimulating elements, and wherein each of the left side return elements is positioned further away from the central axis than its corresponding left side stimulating element, wherein each of the multiple left side return elements is configured to carry electrical current in substantially the second direction; and activating said coil to stimulate a deep region of said subject's brain.

20. The method of claim 19, wherein said neurophysiological condition is at least one of: depression, bipolar disorder, schizophrenia, PTSD, Parkinson's disease, Altzheimer's disease, mild cognitive impairment, autism, Asperger's syndrome, multiple sclerosis, ALS, Tourette's syndrome, blepharospasm, stroke, chronic pain, eating disorder, obesity, anorexia nervosa, bulimia, any addiction including smoking addiction, drug addiction, alcoholism or gambling, ADHD, OCD, epilepsy, migraine, tinnitus.

\* \* \* \* \*